United States Patent
Saint-Remy

(10) Patent No.: US 10,023,847 B2
(45) Date of Patent: Jul. 17, 2018

(54) IMMUNOGENIC PEPTIDES FOR USE IN THE PREVENTION AND/OR TREATMENT OF INFECTIOUS DISEASES, AUTOIMMUNE DISEASES, IMMUNE RESPONSES TO ALLOFACTORS, ALLERGIC DISEASES, TUMORS, GRAFT REJECTION AND IMMUNE RESPONSES AGAINST VIRAL VECTORS USED FOR GENE THERAPY OR GENE VACCINATION

(75) Inventor: Jean-Marie Saint-Remy, Grez-Doiceau (BE)

(73) Assignee: IMNATE SARL, Strassen (LU)

( * ) Notice: Subject to any disclaimer, the term of this patent is extended or adjusted under 35 U.S.C. 154(b) by 989 days.

(21) Appl. No.: 13/988,925

(22) PCT Filed: Nov. 24, 2011

(86) PCT No.: PCT/EP2011/070898
§ 371 (c)(1),
(2), (4) Date: Jun. 6, 2013

(87) PCT Pub. No.: WO2012/069568
PCT Pub. Date: May 31, 2012

(65) Prior Publication Data
US 2013/0259885 A1    Oct. 3, 2013

(30) Foreign Application Priority Data
Nov. 25, 2010 (EP) .................................. 10192559

(51) Int. Cl.
| A61K 39/00 | (2006.01) |
| A61K 35/17 | (2015.01) |
| A61K 39/35 | (2006.01) |
| A61K 39/385 | (2006.01) |
| C12N 5/0783 | (2010.01) |
| C12N 9/02 | (2006.01) |
| C12N 9/90 | (2006.01) |
| A61K 39/12 | (2006.01) |
| C07H 21/00 | (2006.01) |

(52) U.S. Cl.
CPC ............ *C12N 9/0051* (2013.01); *A61K 35/17* (2013.01); *A61K 39/0008* (2013.01); *A61K 39/0011* (2013.01); *A61K 39/12* (2013.01); *A61K 39/35* (2013.01); *A61K 39/385* (2013.01); *C12N 5/0646* (2013.01); *C12N 9/90* (2013.01); *C12Y 503/04001* (2013.01); *A61K 2039/5158* (2013.01); *A61K 2039/55505* (2013.01); *A61K 2039/57* (2013.01); *A61K 2039/6031* (2013.01); *A61K 2039/627* (2013.01); *C07K 2319/40* (2013.01); *C12N 2710/10334* (2013.01)

(58) Field of Classification Search
None
See application file for complete search history.

(56) References Cited

U.S. PATENT DOCUMENTS

| 4,599,231 A | 7/1986 | Milich et al. |
| 5,589,175 A | 12/1996 | Vahlne et al. |
| 6,656,471 B1 | 12/2003 | Sastry et al. |
| 7,306,804 B2 | 12/2007 | Sastry et al. |
| 2005/0032039 A1 | 2/2005 | Sastry et al. |
| 2006/0182763 A1 | 8/2006 | Kim et al. |
| 2010/0303866 A1 | 12/2010 | Saint-Remy |
| 2010/0330088 A1 | 12/2010 | Saint-Remy |

FOREIGN PATENT DOCUMENTS

| JP | S61-501705 A | 8/1986 |
| JP | H06-501260 A | 2/1994 |
| JP | 2002-529112 A | 9/2002 |
| JP | 2010-500308 A | 1/2010 |
| WO | WO-85/04103 A1 | 9/1985 |
| WO | WO-92/05800 A1 | 4/1992 |
| WO | WO-00/29008 A2 | 5/2000 |
| WO | WO-2005/039613 A1 | 5/2005 |
| WO | WO-2007/135684 A2 | 11/2007 |
| WO | WO-2008017517 A1 | 2/2008 |
| WO | WO-2009/100505 A1 | 8/2009 |
| WO | WO-2009/101205 A2 | 8/2009 |
| WO | WO-2009/101206 A2 | 8/2009 |
| WO | WO-2009/101208 A2 | 8/2009 |
| WO | WO-2009101206 A2 | 8/2009 |
| WO | WO-2009101206 A3 | 8/2009 |
| WO | WO-2009/106073 A2 | 9/2009 |
| WO | WO-2010/037395 A2 | 4/2010 |

OTHER PUBLICATIONS

Girardi et al (JBC, 2016, 291 (20): 10677-10683).*
Notice on the Third Office Action for Chinese Patent Application No. 201180056725.7, dated Oct. 29, 2015 (10 pages) (English language translation provided).
Communication pursuant to Article 94(3) EPC for European Patent Application No. 11787873.6, dated Jan. 21, 2016 (6 pages).
Notice of Grounds of Rejection for Japanese Patent Application No. 2013-540353, dated Jan. 5, 2016 (English language translation provided, 9 pages).
Apostolou et al., "Evidence for two subgroups of CD4-CD8- NKT cells with distinct TCR alpha beta repertoires and differential distribution in lymphoid tissues," J Immunol. 165(5):2481-90 (2000).
Ho et al., "CD4(-)CD8alphaalpha subset of CD1d-restricted NKT cells controls T cell expansion," J Immunol. 172(12):7350-8 (2004).
Patent Examination Report No. 1 for Australian Patent Application No. 2011333749, dated Feb. 5, 2016 (8 pages).
Official Action for Russian Patent Application No. 2013128866, dated Feb. 24, 2016 (English language translation provided) (10 pages).
Balato et al., "Natural killer T cells: An unconventional T-cell subset with diverse effector and regulatory functions," *Journal of Investigative Dermatology* 129: 1628-1642 (2009).
Castaño et al., "Peptide binding and presentation by mouse CD1," *Science* 269: 223-226 (1995).
Zeng at al., "Crystal structure of mouse CD1: An MHC-like fold with a large hydrophobic binding groove," *Science* 277: 399-345 (1997).

(Continued)

Primary Examiner — Gerald R Ewoldt
Assistant Examiner — Marianne Dibrino
(74) Attorney, Agent, or Firm — Clark & Elbing LLP

(57) ABSTRACT

The invention describes new peptides containing epitopes recognized by CD4+ natural killer T (NKT) cells for increasing activity for use in infectious diseases, autoimmune diseases, immune reaction to administration of allofactors, allergic diseases, therapy of tumors, prevention of graft rejection and prevention of immunization against viral proteins used in gene therapy or gene vaccination.

8 Claims, 4 Drawing Sheets

(56) References Cited

OTHER PUBLICATIONS

Figure 1:
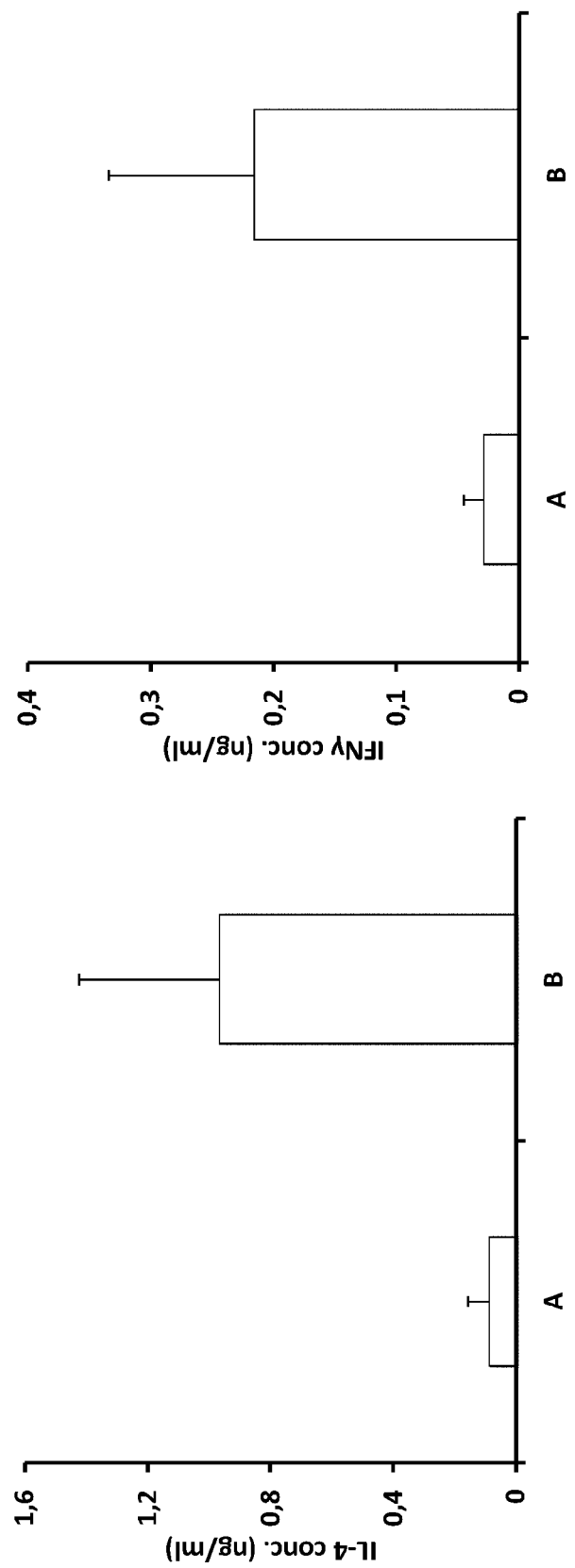
Figure 2:
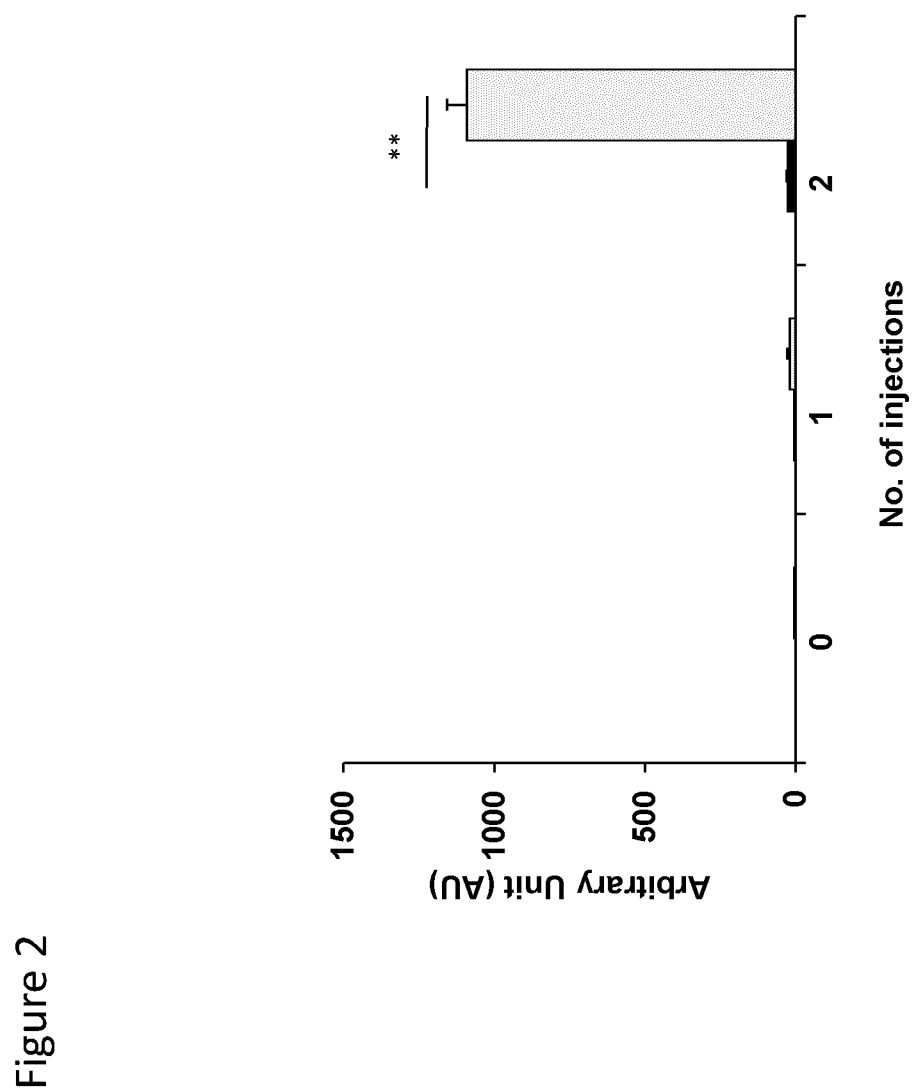

International Search Report for International Patent Application No. PCT/EP2011/070898, dated Jul. 30, 2012 (4 pages).
Written Opinion of the International Searching Authority for International Patent Application No. PCT/EP2011/070898, dated Jul. 30, 2012 (6 pages).
Notice on the Second Office Action for Chinese Patent Application No. 201180056725.7, dated Apr. 16, 2015 (10 pages) (English language translation provided).
Zeng at al., "Crystal structure of mouse CD1: An MHC-like fold with a large hydrophobic binding groove," *Science* 277: 339-345 (1997).
Notice on the First Office Action for Chinese Patent Application No. 201180056725.7, dated Aug. 22, 2014 (16 pages) (English language translation provided).
Official Action for Russian Patent Application No. 2013128866/10(042968), dated Oct. 29, 2015 (13 pages) (English language translation included).
Patent Examination Report No. 2 for Australian Patent Application No. 2011333749, dated Jul. 11, 2016 (5 pages).
Chuanlin Yu ed., Molecular Immunology, Fudan University Press, Shanghai Medical College Press; publication date: May 2001; pp. 428-429, 433-436 (English language translation provided) (15 pages).
Wang et al., "Generation and characterization of HLA-A*2.1 restricted and Prostein 31-39 specific NKT cell lines," Acta Academiae Medicine Militaris Tertiae. 28(16):1652-1655 (2006) (English language translation provided) (11 pages).
Notice on the Fifth Office Action for Chinese Patent Application No. 201180056725.7, dated Dec. 13, 2016 (13 pages) (English language translation provided).

* cited by examiner

IMMUNOGENIC PEPTIDES FOR USE IN THE PREVENTION AND/OR TREATMENT OF INFECTIOUS DISEASES, AUTOIMMUNE DISEASES, IMMUNE RESPONSES TO ALLOFACTORS, ALLERGIC DISEASES, TUMORS, GRAFT REJECTION AND IMMUNE RESPONSES AGAINST VIRAL VECTORS USED FOR GENE THERAPY OR GENE VACCINATION

CROSS-REFERENCE TO RELATED APPLICATION

This application is the U.S. national stage filing under 35 U.S.C. § 371 of International Application No. PCT/EP2011/070898, filed Nov. 24, 2011, which claims the benefit of the filing date of European Patent Application No. 10192559.2, filed Nov. 25, 2010.

FIELD OF THE INVENTION

The present invention relates to immunogenic peptides and their use in treating infectious diseases, autoimmune diseases, immune responses towards allofactors, allergic diseases, tumor, graft rejection and immune responses against viral vectors used for gene therapy or gene vaccination

BACKGROUND OF THE INVENTION

The therapy of many diseases in mammals is limited by the absence of specific medicaments.

In infections caused by intracellular pathogens infection persists because of the insufficiency of immune response which would recognize and eliminate infected cells. Many pathogens reduce the surface expression of molecules such as the major histocompatibility complex of class I (class I MHC) in the cells invaded by said pathogens, thereby reducing the capacity of the immune system to elicit a cytolytic immune response which is elicited when T lymphocytes of the CD8+ lineage recognize and are activated by class I MHC presenting pathogen-derived epitopes. An alternative strategy by which cytolytic lymphocytes could eliminate cells invaded by a pathogen would be much desirable. Such a strategy has been proposed (EP 2 059 256) in which class II restricted epitopes derived from intracellular pathogens and coupled to a thiol-oxidoreductase motif are used to elicit cytolytic CD4+ T cells which induce apoptosis of the antigen-presenting cell (APC) presenting the cognate epitope. However, the recruitment and activation of an alternative subset of cytolytic T cells would represent a distinct possibility to increase elimination of cells infected with an intracellular pathogen.

In autoimmune diseases, as in immune responses to administration of an allofactor and in allergic diseases, it is advantageous to eliminate cells presenting peptides from an autoantigen, an allofactor or an allergen, so as to prevent any unwanted immune responses and thereby diseases associated with such unwanted immune responses. Under such circumstance epitopes from autoantigens, allofactors or allergens are primarily presented by class II MHC and the complex formed between the epitope and class II determinants activated T lymphocytes of the CD4+ lineage. This results in activation of B lymphocytes and production of antibodies to said autoantigens, allofactors or allergens. A method which would result in eliminating of APC by cytolysis would prevent CD4+ T cell activation and thereby the production of antibodies. Such a strategy has been proposed and described in patent application WO 2008/017517 A1 in which class II restricted epitopes of autoantigens or allergens, or of allofactors, respectively, are used attached to a thiol-oxidoreductase motif. Cytolytic class II-restricted CD4+ T cells elicited by exposure to class II restricted epitopes coupled to said motif induce apoptosis of APC presenting the cognate epitope. However, the recruitment and activation of alternative cytolytic T cells would represent a valuable alternative strategy.

In the case of tumors, cells escape elimination by down-regulating surface expression of class I and class II MHC determinants. Any strategy by which cytolytic T cells specific to tumor antigens would be elicited would therefore represent a much desirable strategy for the treatment of tumors. WO 2009/101205 teaches that cytolytic T cells activated by class II restricted presentation of tumor derived antigens is of use for tumor elimination. However, this approach is limited by the poor expression of MHC class II determinants by tumors.

In graft rejection, the process of chronic rejection is driven by the indirect presentation of antigens shed by the graft and presented by the recipient antigen-presenting cells to his/her own T lymphocytes. The indirect presentation occurs by presentation of graft derived epitopes by both class I and class II epitopes. T lymphocytes of the CD8 lineage activated by class I MHC presentation of graft antigens migrate to the graft wherein they mediate rejection by recognition of their cognate epitopes directly on grafted cells. Yet activation of CD8 cells require help from CD4 cells activated by indirect presentation of graft derived antigens by class II MHC determinants. WO 2009/100505 teaches that the use of class II restricted T cell epitopes derived from the graft and coupled to a thiol-oxidoreductase motif allows elimination by apoptosis of APC participating in indirect presentation. However, an alternative strategy by which another subset of cytolytic T cells would be generated would be much desirable.

Likewise, novel therapeutic approaches such as gene therapy and gene vaccination are severely limited by the host immune response to viral vectors used for transgenesis or vaccination. In both these situations, antigens derived from viral vectors are shed by cells transduced with the vector and presented to host lymphocytes by host APC, namely by indirect antigen presentation. To note is the fact that many viral vectors activate not only the adaptive immune system, leading to the production of specific antibodies and specific T cell activation, but said viral vectors also activate the innate immune system. Activation of innate immunity serves as an adjuvant for the adaptive response. WO 2009/101204 teaches that class II restricted epitopes derived from viral vectors and coupled to a thiol-oxidoreductase motif can elicit the activation of cytolytic class II restricted CD4 T cells. However, an alternative strategy is highly desirable, which would suppress activation of the innate immune system.

In all examples enumerated herein, it is obvious for the one skilled in the art that alternative strategies by which antigen-specific cytolytic T cells could be elicited, which would eliminate in an antigen-specific manner APC presenting said specific antigen, would be of much value.

The present invention presents such an alternative strategy.

Natural killer T (NKT) cells constitute a distinct subset of non-conventional T lymphocytes that recognize antigens presented by the non-classical MHC complex molecule CD1d. Two subsets of NKT cells are presently described.

Type 1 NKT cells, also called invariant NKT cells (iNKT), are the most abundant. They are characterized by the presence of an alpha-beta T cell receptor (TCR) made of an invariant alpha chain, Valpha14 in the mouse and Valpha24 in humans. This alpha chain is associated to a variable though limited number of beta chains. Type 2 NKT cells have an alpha-beta TCR but with a polymorphic alpha chain. However, it is apparent that other subsets of NKT cells exist, the phenotype of which is still incompletely defined, but which share the characteristics of being activated by glycolipids presented in the context of the CD1d molecule.

NKT cells typically express a combination of natural killer (NK) cell receptor, including NKG2D and NK1.1. NKT cells are part of the innate immune system, which can be distinguished from the adaptive immune system by the fact that they do not require expansion before acquiring full effector capacity. Most of their mediators are preformed and do not require transcription. NKT cells have been shown to be major participants in the immune response against intracellular pathogens and tumor rejection. Their role in the control of autoimmune diseases and of transplantation rejection is also advocated.

The recognition unit, the CD1d molecule, has a structure closely resembling that of the MHC class I molecule, including the presence of beta-2 microglobulin. It is characterized by a deep cleft bordered by two alpha chains and containing highly hydrophobic residues, which accepts lipid chains. The cleft is open at both extremities, allowing to accommodate longer chains. The canonical ligand for CD1d is the synthetic alpha galactosylceramide (alpha GalCer). However, many natural alternative ligands have been described, including glyco- and phospholipids, the natural lipid sulfatide found in myelin, microbial phosphoinositol mannoside and alpha-glucuronosylceramide. The present consensus in the art (see reviews, such as Matsuda et al, Current Opinion in Immunology 2008, 20:358-368 and Godfrey et al, Nature reviews Immunology 2010, 11: 197-206) is that CD1d binds only ligands containing lipid chains, or in general a common structure made of a lipid tail which is buried into CD1d and a sugar residue head group that protrudes out of CD1d.

Peptides are not deemed to be able to activate NKT cells through presentation by CD1d. It was, however, suggested that long hydrophobic peptides containing bulky aminoacid residues could bind to CD1d (Castano et al, Science 1995, 269: 223-226). Observations carried out using phage display libraries expressing random sequence peptides with no defined physiological relevance, allowed establishing a theoretical consensus motif (Castano et al, Science 1995, 269: 223-226 and see below).

In fact, Castano et al showed that the cells which are activated are CD8+ T cells, namely MHC class I restricted cells, and not NKT cells. These findings teach the one skilled in the art that there is no evidence that hydrophobic peptides are presented by CD1d molecules. The physiological relevance of the claims made by Castano et al was further questioned due to the inability to elicit NKT cells under conventional immunization protocols (Matsuda et al, Current Opinion in Immunology 2008, 20:358-368 and Brutkiewicz Journal of Immunology 2006, 177: 769-775). Artificial systems such as immunization with cells transfected to overexpress CD1d and loaded in vitro with an ovalbumin-derived peptide were able to elicit NKT cells. Likewise, intradermal immunization with plasmid DNA together with murine CD1d and costimulatory molecules induce cytolytic CD1d-restricted T cells (Lee et al, Journal of Experimental Medicine 1998, 187: 433-438). Hydrophobic peptides containing a structural motif made of an aromatic residue in position P1 and P7, which represent anchoring residues for binding to CD1d hydrophobic pockets located at each end of the CD1d molecule and an aliphatic chain in position P4 were claimed by Castano et al (Science 269: 223, 1995) to contain a core motif for CD1d binding epitopes. As described above, the conclusions reached by Castano et al are not supported by data.

We made the unexpected finding that peptides encompassing an hydrophobic aminoacid sequence are in fact capable of eliciting activation of NKT cells. An example of such sequence is represented by the motif [FW]-xx-[ILM]-xx-[FW], wherein [FW] is an aminoacid selected from phenylalanine or tryptophan, and [ILM] is an aminoacid selected from isoleucine, leucine or methionine. [FW] in P7 is said to be permissive, meaning that T or H can substitute either for F or W.

We further discovered that a CD1d binding motif was particularly efficient in modulating NKT activity when coupled to a thiol-oxidoreductase motif. This motif presents a general structure of C-XX-C in which C is cysteine and X is any aminoacid except tyrosine, phenylalanine and tryptophan. Patent application WO 2008/017517 A1 teaches that class II restricted T cell epitopes coupled to a thiol-oxidoreductase motif acquire the property of transforming the phenotype and the function of class II restricted CD4 T cells into potent cytolytic cells, inducing apoptosis of APC. This effect is due to increased synapse formation between APC and T cells, a consequence of the reduction and isomerization of the CD4 molecule at the surface of T cells.

A large majority of NKT cells carry the CD4 co-receptor, the role of which remains ill defined. A recent publication, however, suggested that CD4 binds to the CD1d molecule much in the same way as its binding to WIC class II (Thedrez et al Blood 110: 251-258, 2007). In addition the presence of CD4 was shown to be required for full activation of NKT cells.

The present invention therefore relates to the use of hydrophobic peptides having the capacity to bind to CD1d and thereby recruit and activate NKT cells, coupled to a thiol-oxidoreductase motif. Such peptides ensure antigen-specificity and represent a valuable approach for the treatment of (1) infectious diseases with intracellular pathogens, in which infected cells present hydrophobic peptides derived from the pathogen and bound to CD1d. Increased NKT recruitment and/or activity of such NKT cells would therefore concur to the elimination of infected cells;

(2) autoimmune diseases, immune responses to administration of an allofactor and allergic diseases, in which antigens associated to each of these 3 types of diseases generate hydrophobic peptides presented by CD1d. Increased recruitment and/or activity of antigen-specific NKT cells could therefore help in eliminating antigen-presenting cells and thereby eliminate an unwanted immune response;

(3) tumors, as tumor cells often express CD1d carrying tumor-specific antigens, which can be recognized by NKT cells. Increasing the activity and recruitment of such NKT cells would lead to increased tumor elimination;

(4) graft rejection, as host antigen-presenting cells present hydrophobic peptides derived from the graft in the context of CD1d. Recognition of these peptides by host NKT cells would lead to elimination of the antigen-presenting cells and abort the chronic graft rejection process;

(5) gene therapy and gene vaccination, wherein antigens from viral vectors and shed by transduced cells are presented by CD1d determinants. Recruitment and activation of NKT cells eliminating host APC through recognition of viral vector antigens would be beneficial both for persistence of transgene expression and maintenance of full immunogenicity of the transgene in gene vaccination.

In addition to the therapeutic interest of the present invention, we made the unexpected observation that addition of an oxidoreductase motif within flanking residues of CD1d epitopes increases TCR binding, which results in a much improved detection of CD4+ NKT cells. Peptides encompassing natural CD1d-restricted epitopes and at least one thioreductase motif of the CxxC format, in which C stands for cysteine and x for any aminoacids except cysteine or bulky residues, as described in the present invention, have therefore a major interest for:

(1) analytical purposes: detection of NKT cell precursor frequency before vaccination, evaluation of peptide binding affinity for CD1d complexes, follow-up of specific NKT cells during the course of vaccination or under immunosuppression, identification of cells regardless of their biological activity, identification of cells implicated in the mechanism of disease, depletion of specific NKT cells, and detection of NKT cells in situ, such in organ biopsies;

(2) preparative purposes: preparation of specific NKT cells for evaluation of function and preparation of NKT cells for culture and purification;

(3) quality control for cell population aimed at cell therapy;

(4) therapeutic purposes, including depletion of specific CD4+ NKT cells before organ grafting.

SUMMARY OF THE INVENTION

The present invention relates to the use of isolated immunogenic peptides for the prevention and treatment of infection with an intracellular pathogen in a subject by increasing the immune response towards specific antigens derived from said intracellular pathogen.

The present invention also relates to the use of isolated immunogenic peptides for the prevention and treatment of autoimmune responses, immune responses to administration of allofactors and immune responses to exposure to allergens.

The present invention further relates to the use of isolated immunogenic peptides for the treatment of tumors.

The present invention also relates to the use of isolated immunogenic peptides for the prevention of graft rejection.

The present invention also relates to the use of isolated immunogenic peptides for the prevention of immune response against viral proteins used for gene therapy and/or gene vaccination.

The present invention also relates to peptides for the detection, preparation and depletion of NKT cells.

The present invention relates in one aspect to the use of at least one isolated immunogenic peptide comprising (i) a NKT cell epitope derived from a pathogen-associated antigen and (ii) a thiol-oxidoreductase motif (thioredox motif in short) as a medicament for preventing and/or treating, in a subject, infection with said pathogen.

In a further aspect, the invention also covers the use of at least one isolated immunogenic peptide comprising (i) a NKT cell epitope derived from an autoantigen, an allofactor or an allergen and (ii) a thioredox motif as a medicament for preventing and/or treating, in a subject, immune responses against autoantigens, allofactors and/or allergens.

In yet a further aspect, the invention also covers the use of at least one isolated immunogenic peptide comprising (i) a NKT cell epitope derived from a tumor-associated antigen and (ii) a thioredox motif as a medicament for treating, in a subject, a tumor.

In yet a further aspect, the invention also covers the use of at least one isolated immunogenic peptide comprising (i) a NKT cell epitope derived from an alloantigen and (ii) a thioredox motif as a medicament for preventing, in a subject, rejection of a graft.

In yet a further aspect, the invention also covers the use of at least one isolated immunogenic peptide comprising (i) a NKT cell epitope derived from a viral vector for gene therapy or gene vaccination and (ii) a thioredox motif as a medicament for preventing, in a subject, an immune response against the viral vector.

In a further aspect, the invention also covers the use of at least one isolated immunogenic peptide comprising (i) a NKT cell epitope derived from a pathogen-associated antigen, an autoantigen, allofactor, allergen, a tumor-associated antigen, an alloantigen or a viral vector antigen, and (ii) a thioredox motif, as a medicament for increasing the activation, cytokine production and cytolytic activity of CD4+ NKT cells in said subject.

Generally, the invention provides immunogenic peptides comprising (i) a NKT-cell epitope derived from a pathogen-associated antigen, an autoantigen, allofactor, allergen, a tumor-associated antigen, an alloantigen, or a viral vector antigen, and (ii) a thioredox motif for use in preventing or treating an infection with an intracellular pathogen, preventing or treating an immune response against autoantigens, allofactors, allergens, treating tumors, preventing immunization against alloantigens or against a viral vector antigen, in a recipient by increasing the CD4+ NKT cell response in said recipient.

The present invention also relates to NKT cells of either type 1 (iNKT) or type 2 subset, as well as less characterized NKT subsets, all characterized as carrying the CD4 co-receptor and a TCR beta chain capable to recognize the CD1d bound peptide.

The present invention also relates to hydrophobic peptides able to bind to CD1d for presentation to NKT cells.

The present invention relates to hydrophobic peptides encompassing at least one CD1d-restricted T cell epitope. The structure of the CD1d molecule indicates that hydrophobic aminoacid residues are required to occupy the two hydrophobic pockets located at the extremities of the CD1d cleft and that an aliphatic residue should occupy the position in the middle of the cleft. Therefore, as a general example of CD1d binding sequence, the motif [FW]-xx-[ILM]-xx-[FWTH] can be used in which [FW] indicates that either F or W can occupy the first anchoring residue (P1), that the P4 position can be occupied by either I, L or M and that P7 can be occupied by F, W, T or H. x in this general model motif stands for any aminoacid. It should be clear for the one skilled in the art that various combinations of these aminoacid residues are possible. In a particular embodiment the general model motif can be presented as a reverted sequence such as [FWTH]-xx-[ILM]-xx-[FW].

Said thioredox motif is made of a consensus sequence ([CST]-XX-[CST]), wherein [CST] is an amino acid selected from cysteine, serine and threonine, and X can be any amino acid except tyrosine (Y), phenylalanine (F) and tryptophan (W). Said thioredox motif is added to the peptide at either amino-terminal or carboxy-terminal end, or on each terminal end, potentially separated from the said CD1d-restricted T cell epitope by a linker of in between 1 to 7 aminoacids.

In a particular embodiment, said linker comprises aminoacids which are part of the natural flanking residues.

The invention further relates to methods for obtaining or inducing populations of NKT cells as described above, said methods comprising the steps of:

(i) providing isolated natural CD4+ T cells;

(ii) contacting those cells with an immunogenic peptide comprising a T cell epitope presented by the CD1d molecule and, adjacent to said T cell epitope or separated there from by a linker of at most 7 aminoacids, a C-XX-[CST] or [CST]-XX-C motif; and (iii) expanding said cells in the presence of IL-2/IL-15 and/or IL-7

In a further aspect, the invention encompasses a method of identifying a population of CD4+ NKT cells, said method comprising the steps of:

(i) providing isolated natural CD4+ T cells;

(ii) providing CD4+ T cells suspected of being cytotoxic; and (iii) determining that the T cells provided in (ii) display, compared to the T cells provided in (i), the characteristics described above.

In any of the above uses said intracellular pathogen-associated antigen may be any antigen derived from viruses, bacteria, mycobacteria or parasites with an intracellular life cycle.

In any of the above, said autoantigen may be any antigen associated with an autoimmune disease. Examples of such diseases are insulin-dependent diabetes, multiple sclerosis, myasthenia gravis and thyroiditis.

In any of the above, said allofactors are polypeptides or proteins and factors used for replacement therapy for coagulation defects or fibrinolytic defects, including factor VIII, factor IX and staphylokinase, hormones such as insulin and growth hormone, cytokines and growth factors such as interferon-alpha, interferon-beta, interferon-gamma, GM-CSF and G-CSF, antibodies for the modulation of immune responses, including anti-IgE antibodies in allergic diseases, anti-CD3, anti-CD4 and anti-CD20 antibodies in graft rejection and in a variety of auto-immune diseases, anti-TNF-alpha antibodies in rheumatoid arthritis, and erythropoietin in renal insufficiency.

In any of the above, said allergen being airborne allergen such as those derived from house dust mite, from pollens or from domestic animals, food allergens such as peanut, ovalbumin, cereals, fruits and legumes, and contact antigens such as latex. Diseases characterizing allergen sensitization include allergic asthma, allergic rhino-sinusitis, anaphylactic shock, urticaria, atopic dermatitis and contact dermatitis.

In any of the above, said tumor-associated antigens being an oncogene, a proto-oncogene, a virus-derived protein, a surviving factor or a clonotypic determinant such as an idiotypic determinant derived from a B cell receptor.

In any of the above, said alloantigens being major histocompatibility antigens, minor histocompatibility antigens or tissue specific antigens. Said antigens are involved in cellular and tissue graft rejection.

In any of the above, said viral vectors being derived from adenovirus, adeno-associated virus, retrovirus or lentivirus.

In any of the above uses said thioredox motif may be adjacent to said NKT cell epitope or be separated from said NKT cell epitope by a linker. In particular embodiments, the linker consists of at most 7 amino acids.

In a further embodiment of the immunogenic peptide in the above uses, said thioredox motif does not occur naturally within a region of 8 amino acids N- or C-terminally adjacent to the NKT-cell epitope in said pathogen-associated antigen, auto-antigen, allofactor, allergen, tumor-associated antigen, alloantigen or viral vector antigen. In particular said thioredox motif is positioned N-terminally of the NKT-cell epitope.

In particular embodiment of the immunogenic peptide for the above uses, the immunogenic peptide further comprises and endosomal targeting sequence. Any of the above immunogenic peptides may be produced by chemical synthesis or by recombinant expression.

A further method of the invention aims at obtaining a population of NKT cells, said method comprising the steps of:

(i) providing an immunogenic peptide comprising a NKT cell epitope derived from an intracellular pathogen-associated antigen, an autoantigen, an allofactor, an allergen, a tumor-associated antigen, an alloantigen or a viral vector antigen, and (ii) a thioredox motif;

(ii) administering the immunogenic peptide to a subject; and (in the presence of an adjuvant)

(iii) obtaining a population of CD4+ NKT cells.

Populations of CD4+ NKT cells obtainable by the above methods are also part of the invention, as well as their use as a medicament for preventing or treating, in a subject, infection with said intracellular pathogen, preventing or treating an autoimmune disease, an immune response to an allofactor, preventing or treating allergic diseases, treating tumors, preventing graft rejection, and preventing an immune response to a viral vector used for gene therapy or gene vaccination.

A further aspect of the invention relates to isolated immunogenic peptides comprising a NKT-cell epitope derived from an intracellular pathogen-associated antigen, or from an autoantigen, an allofactor, an allergen, a tumor-associated antigen, an alloantigen or a viral vector antigen, and, adjacent to the NKT-cell epitope or separated from the NKT-cell epitope by a linker, a thioredox motif.

Yet a further aspect of the invention relates to isolated peptide comprising a NKT-cell epitope derived from an intracellular pathogen-associated antigen, or from an autoantigen, an allofactor, an allergen, a tumor-associated antigen, an alloantigen or a viral vector antigen, and, adjacent to the NKT-cell epitope or separated from the NKT-cell epitope by a linker, a thioredox motif, for the detection, preparation or depletion of NKT cells.

The invention further encompasses isolated viral vectors characterized in that they comprise at least one pathogen-associated antigen, or at least one autoantigen, or at least one allofactor, or at least one allergen, or at least one tumor-associated antigen, or at least one alloantigen, or at least one viral vector antigen comprising a NKT-cell epitope and adjacent to said NKT-cell epitope or separated from the NKT-cell epitope by a linker, a thioredox motif.

More particularly, the invention provides isolated viral vectors characterized in that at least one NKT-cell epitope present in at least one of the pathogen-associated antigens, or of the autoantigen, or of allofactor, or of allergen, or of a tumor-associated antigen, or of an alloantigen, or of a viral vector antigen is modified by insertion in said pathogen-associated antigen, said autoantigen, said allofactor, said allergen, said tumor-associated antigen, said alloantigen, or said viral vector antigen, adjacent to said NKT-cell epitope or separated from said NKT-cell epitope by a linker, of a thioredox motif.

DEFINITIONS

The term "peptide" when used herein refers to a molecule comprising an amino acid sequence of between 2 and 200 amino acids, connected by peptide bonds, but which can in a particular embodiment comprise non-amino acid structures (like for example a linking organic compound). Peptides according to the invention can contain any of the conventional 20 amino acids or modified versions thereof, or can contain non-naturally occurring amino acids incorporated by chemical peptide synthesis or by chemical or enzymatic modification.

The terms "peptide" or "immunogenic peptide" are used indifferently, but "immunogenic peptide" is usually preferred for peptide used for therapeutic purposes, whilst "peptide" is preferred for the detection, preparation and depletion of NKT cells.

The term "epitope" when used herein refers to one or several portions (which may define a conformational epitope) of a protein which is/are specifically recognized and bound by an antibody or a portion thereof (Fab', Fab2', etc.) or a receptor presented at the cell surface of a B or T cell lymphocyte, and which is able, by said binding, to induce an immune response.

The term "antigen" when used herein refers to a structure of a macromolecule comprising one or more hapten(s) and/or comprising one or more T cell epitopes. Typically, said macromolecule is a protein or peptide (with or without polysaccharides) or made of proteic composition and comprises one or more epitopes; said macromolecule can herein alternatively be referred to as "antigenic protein" or "antigenic peptide".

The term "T cell epitope" or "T-cell epitope" in the context of the present invention refers to a dominant, sub-dominant or minor T cell epitope, i.e., a part of an antigenic protein that is specifically recognized and bound by a receptor at the cell surface of a T lymphocyte. Whether an epitope is dominant, sub-dominant or minor depends on the immune reaction elicited against the epitope. Dominance depends on the frequency at which such epitopes are recognized by T cells and able to activate them, among all the possible T cell epitopes of a protein. In particular, a T cell epitope is an epitope bound by MHC class I or MHC class II molecules.

The term "NKT cell epitope" refers to a part of an antigenic protein that is specifically recognized and bound by a receptor at the cell surface of a T lymphocyte. In particular, a NKT cell epitope is an epitope bound by CD1d molecules.

The term "CD4+ effector cells" refers to cells belonging to the CD4-positive subset of T-cells whose function is to provide help to other cells, such as, for example B-cells. These effector cells are conventionally reported as Th cells (for T helper cells), with different subsets such as Th0, Th1, Th2, and Th17 cells.

The term "NKT cells" refers to cells of the innate immune system characterized by the fact that they carry receptors such as NK1.1 and NKG2D, and recognize epitopes presented by the CD1d molecule. In the context of the present invention, NKT cells can belong to either the type 1 (invariant) or the type 2 subset, or to any of the less characterized NKT cells with more polymorphic T cell receptors than type 1 or type 2 NKT cells.

The "CD1d molecule" refers to a non-MHC derived molecule made of 3 alpha chains and an anti-parallel set of beta chains arranged into a deep hydrophobic groove opened on both sides and capable of presenting lipids, glycolipids or hydrophobic peptides to NKT cells.

The term "immune disorders" or "immune diseases" refers to diseases wherein a reaction of the immune system is responsible for or sustains a malfunction or non-physiological situation in an organism. Immune disorders in the context of the present invention refer to pathology induced by infectious agents and tumor surveillance.

The term "allofactor" refers to a protein, peptide or factor (i.e. any molecule) displaying polymorphism when compared between two individuals of the same species, and, more in general, any protein, peptide or factor that induces an (alloreactive) immune response in the subject receiving the allofactor.

The term "alloantigen" or "allograft antigen" when used herein refer to an antigen derived from (shed from and/or present in) a cell or tissue which, when transferred from a donor to a recipient, can be recognized and bound by an antibody of B or T-cell receptor of the recipient. Alloantigens are typically products of polymorphic genes. An alloantigen is a protein or peptide which, when compared between donor and recipient (belonging to the same species), displays slight structural differences. The presence of such a donor antigen in the body of a recipient can elicit an immune response in the recipient. Such alloreactive immune response is specific for the alloantigen.

The term "thiol-oxidoreductase motif", "thioreductase motif", "thioredox motif" or "redox motif" are used here as synonymous terms and refers to a motif of general sequence made of [CST]-XX-[CST], in which C stands for cysteine, S for serine, T for threonine and X for any aminoacid except tyrosine, phenylalanine or tryptophan.

DETAILED DESCRIPTION OF THE INVENTION

The present invention provides ways to prevent or treat, in a subject, infection with an intracellular pathogen. It further provides ways to prevent and treat autoimmune diseases, immune responses following administration of an allofactor or to allergens. It further provides ways to treat tumors, to prevent graft rejection and to prevent immune response against viral vectors.

In particular, the invention provides ways to augment the expansion and functional activity of CD4+ NKT cells. Such cells are usually classified into two distinct subsets, namely type 1 for NKT cells carrying an invariant TCR alpha chain (Valpha14 in the mouse, Valpha24 in humans), or type 2 NKT cells which have a diverse alpha chain repertoire. However, recent evidence has suggested that alternative subsets of NKT cells which do not fit in the type 1 or type 2 category. It is the purpose of the present invention to include these non conventional NKT cells, provided they carry the CD4 co-receptor. Upon presentation of an antigen bound to CD1d, NKT cells are rapidly activated and secrete a number of cytokines thought to be determinant to influence other cells from both the innate and adaptive immune system, and to exert a potent killing activity of CD1d+ antigen-presenting cell. This mechanism is deemed to be crucial for the defense against infection with intracellular agents, but also in tumor cell surveillance and tumor elimination. The same mechanism is at play for the control of unwanted immune responses as it occurs in auto-immune diseases, immune responses against allofactors or against allergens.

In graft rejection, alloantigens shed from graft are presented to the immune system of the recipient subject by the indirect pathway. This means that shed allograft antigens are taken up by the host antigen-presenting cells, which present said alloantigen to the host T cells in a CD1d-restricted manner. A mechanism by which said host antigen-presenting cells are destroyed by killing after cognate recognition by CD4+ NKT cells is therefore beneficial for the graft recipient.

In immune response towards viral vectors used for gene therapy and gene vaccination, antigens shed from transduced cells are taken up by the host antigen-presenting cells, with subsequent indirect presentation as in the case of graft rejection.

When NKT cells are activated by a peptide modified as to contain a thioreductase activity, the latter increases significantly the properties of NKT cells and thereby increases the killing of cells carrying intracellular microorganisms as well as tumor cells. Killing of cells presenting autoantigens, allofactors or allergens by antigen-specific CD4+ NKT cells suppresses the immune response against said autoantigens, allofactors or allergens. Killing of host cells presenting antigens derived from a graft or from transduced cells aborts the rejection or the response to the viral vector antigen, respectively.

Thus, in a growing number of infectious diseases, the importance of NKT cells has been evidenced. These include infections with mycobacteria (including *mycobacterium tuberculosis*), parasites such as *Leishmania*, bacteria such as *Listeria monocytogenes, salmonella, pseudomonas aeruginosa, streptococcus pneumoniae* and *Borrelia*, and viruses such as herpes simplex virus (Chiba et al Journal of Immunology 181: 2292-2302, 2008; Mattner et al Nature 434: 525529, 2005; Tupin et al Nature Reviews. Microbiology 5: 405-417, 2007). In addition to direct killing of infected cells, NKT cells, by virtue of their capacity to produce high concentrations of cytokines, and in particular IFN-gamma, can trigger non-specific killing mechanisms within the infected cells. These mechanisms include the induction of indoleamine oxidase, nitric oxide synthase and the production of reactive oxygen species.

The participation of NKT cells in the control of immune responses in auto-immune diseases, or against allofactors or allergens has been reported on a number of occasions (Jahng et al Journal of experimental Medicine 199: 947-957, 2004; Van Belle and von Herrath, Molecular Immunology 47: 8-11, 2009) but relatively difficult to describe. In the context of the present invention, we made the unexpected observation that peptides can be presented by the CD1d molecule. A characteristic of the CD1d molecule is to be made of 2 anti-parallel alpha chains forming a cleft sitting atop of a platform made of two anti-parallel beta chains. The cleft is narrow and deep and accept only hydrophobic residues, classically deemed to be only lipids. In fact, peptides with hydrophobic residues have the capacity to bind to the CD1d cleft. Besides, as the cleft is open both sides, peptides longer than 7 aminoacids can be accommodated. Hydrophobic peptides carrying the CD1d motif are found in autoantigens, allofactors and allergens, thereby endowing said autoantigen, allofactor or allergen with the capacity to activate CD4+ NKT cells. Direct elimination by killing of cells presenting said autoantigen, allofactor or allergen eliminates the capacity to mount an immune response against these antigens/factors.

NKT cells have been demonstrated to participate to the defense against tumors, either indirectly by producing cytokines able to boost both innate and adaptive response to tumor cells or directly by killing tumor cells presenting lipid epitopes recognized by NKT cells (Crowe et al, Journal of experimental Medicine 196:119-127, 2002; Tachibana et al, Clinical Cancer Research 11: 7322-7327, 2005; Dhodapkar et al, Journal of experimental Medicine 197: 1667-1676, 2003; Song et al, Journal of clinical Investigation 119: 15241536, 2009). Direct killing involves granzyme and perforin production. Experimental tumors such as sarcomas induced by carcinogenetic agents or by deletion of the p53 tumor suppressor gene, as well as spontaneous tumors such as myelomas have been shown to be suppressed by NKT cells. Tumors susceptible to be treated by the present invention include those expressing oncogenes, such as the MAGE identified in some melanomas or tyrosine kinases, such as ALK (anaplastic lymphoma kinase) identified in carcinomas of ectodermal origin, proto-oncogens, such as cyclin D1 expressed on soft tissues carcinomas, such as those of the kidney or parathyroid as well as in multiple myeloma, virus-derived proteins, such as those of the Epstein-Barr virus in some carcinomas and in some Hodgkin-type lymphomas, surviving factors, such as surviving or bcl2, and clonotypic determinants, such as idiotypic determinants derived from B cell receptor in follicular lymphomas or multiple myelomas or T cell receptor determinants in T cell malignancies.

Cells being part of a graft, either tissue graft or cellular graft, do not, or only minimally, carry the CD1d molecule. The same applies for cells transduced in gene therapy or gene vaccination. In both of these situations, unwanted immune responses leading to either graft rejection or immunization towards the viral vector, the response is elicited by indirect antigen presentation by host antigen-presenting cells to host T cells. Direct elimination by killing of host antigen-presenting cells after cognate interaction with NKT cells eliminates the capacity to mount an immune response against alloantigens or viral vector antigens.

The present invention relates to the production of peptides containing hydrophobic residues that confer the capacity to bind to the CD1d molecule. Upon administration, such peptides are taken up by APC, directed to the late endosome where they are loaded onto CD1d and presented at the surface of the APC. Said hydrophobic peptides being characterized by a motif corresponding to the general sequence [FW]-xx-[ILM]-xx-[FWTH] or [FWTH]-xx-[ILM]-xx-[FW,] in which positions P1 and P7 are occupied by hydrophobic residues such as phenylalanine (F) or tryptophan (W). P7 is however permissive in the sense that it accepts alternative hydrophobic residues to phenylalanine or tryptophan, such as threonine (T) or histidine (H). The P4 position is occupied by an aliphatic residue such as isoleucine (I), leucine (L) or methionine (M).

International application WO 2009/101206 discloses immunogenic peptides able to elicit the activation of major histocompatibility class II-restricted CD4+ cells, including peptide CGHCGGFTNMFATWSPSK (SEQ ID NO: 1). It is not known from WO 2009/101206 that peptides have the capacity to bind to the CD1d molecule. The present invention therefore relates to peptides binding to CD1d and activating NKT cells, with the proviso that the peptide is not CGHCGGFTNMFATWSPSK (SEQ ID NO: 1).

The present invention relates to peptides made of hydrophobic residues which naturally constitute a CD1d binding motif. In some embodiment, aminoacid residues of said motif are modified, usually by substitution with residues which increase the capacity to bind to CD1d. In a specific embodiment, motifs are modified to fit more closely with the general motif [FW]-xx-[ILM]-xx-[FWTH]. More particularly, peptides are produced to contain a F or W at position 7.

The peptides of the present invention also contain a thioreductase motif adjacent to the hydrophobic residues or separated from such residues by a linker. Once presented by CD1d molecule, the thioreductase motif enhances the capacity to activate NKT cells, thereby increasing their anti-infectious and/or anti-tumor activity, their capacity to suppress immune responses towards autoantigens, allofactors, allergens, allograft antigens and antigens from viral vectors used in gene therapy or gene vaccination.

A general description of the full motif could therefore be [CST]-XX-[CST]-linker-[FW]-xx-[ILM]-xx-[FWTH] or [FW]-xx-[ILM]-xx-[FWTH]-linker-[CST]-XX-[CST], according to the fact that the thioreductase motif can be added in either amino-terminal or carboxy-terminal end. Addition of a linker is optional. When present such linker can be in between 1 and up to 7 aminoacids. It should be clear to the one skilled in the art that this general description is provided only for a general understanding of the invention.

The present invention also relates to NKT cells obtained and activated in vitro for passive re-administration to a host in order to increase its capacity to eliminate cells infected with a pathogen, cells presenting peptides derived from autoantigens, allofactors or allergens, tumor cells, cells presenting alloantigens shed from grafts or from viral proteins used in gene therapy/gene vaccination. As an alternative to the in vitro stimulation of NKT cells by CD1d positive APC, the invention also applies to methods of transfection or transduction of APC using a genetic construct capable of driving expression of the immunogenic peptide into the late endosome for loading onto CD1d molecule.

In particular, the invention provides ways to expand specific NKT cells, with as a consequence increased activity comprising, but not limited to:

(i) increased cytokine production
(ii) increased contact- and soluble factor-dependent elimination of antigen-presenting cells The result is therefore a more efficient response towards intracellular pathogens, autoantigens, allofactors, allergens, tumor cells and more efficient suppression of immune responses against graft and viral proteins used in gene therapy/gene vaccination.

The present invention also relates to the identification of NKT cells with required properties in body fluids or organs. The method comprises identification of NKT cells by virtue of their surface phenotype, including expression of NK1.1, CD4, NKG2D and CD244. Cells are then contacted with NKT cell epitopes defined as peptides able to be presented by the CD1d molecule. Cells are then expanded in vitro in the presence of IL-2 or IL-15 or IL-7.

The present invention therefore provides peptides containing a CD1d binding motif and a thioreductase motif for the detection, preparation and depletion of NKT cells. In a preferred embodiment, such peptides are loaded on isolated CD1d molecule, either monomeric or, preferably multimeric. The CD1d molecule can be in a soluble form or bound to a solid support.

The present invention should be regarded as a curative therapy administered when either the infection is contracted or the tumor already present. This is due to the fact that NKT cells are not thought to enter into a cycle of memorization. When NKT cells are activated, they expand over a period of a few days, and then the population enters into a contraction phase and possible short-term unresponsiveness. However, under some circumstances, it may become advisable to administer the therapy by active immunization with peptides of the invention in a preventive setting. Examples of these are patients at high risk of contracting an infectious disease, as for instance immediately after contact with an infected individual. The present invention therefore covers also the preventive usage of the therapy, either by active vaccination or by passive transfer of cells.

The present invention relates in one aspect to the use of at least one isolated hydrophobic immunogenic peptide comprising (i) a NKT cell epitope derived from a pathogen-associated antigen and (ii) a thio-oxidoreductase motif (thio-redox motif in short) as a medicament for preventing and/or treating, in a subject, infection with said pathogen.

In a further aspect, the invention also covers the use of at least one isolated hydrophobic immunogenic peptide comprising (i) a NKT cell epitope derived from an autoantigen, an allofactor or and allergen and (ii) a thioredox motif as a medicament for preventing and/or treating, in a subject, immune responses against autoantigens, allofactors and/or allergens.

In yet a further aspect, the invention also covers the use of at least one isolated hydrophobic immunogenic peptide comprising (i) a NKT cell epitope derived from a tumor-associated antigen and (ii) a thioredox motif as a medicament for treating, in a subject, a tumor.

In yet a further aspect, the invention also covers the use of at least one isolated hydrophobic immunogenic peptide comprising (i) a NKT cell epitope derived from an alloantigen and (ii) a thioredox motif as a medicament for preventing, in a subject, rejection of a graft.

In yet a further aspect, the invention also covers the use of at least one isolated hydrophobic immunogenic peptide comprising (i) a NKT cell epitope derived from a viral vector for gene therapy or gene vaccination and (ii) a thioredox motif as a medicament for preventing, in a subject, an immune response against the viral vector.

In a further aspect, the invention also covers the use of at least one isolated immunogenic peptide comprising (i) a NKT cell epitope derived from a pathogen-associated antigen, an autoantigen, allofactor, allergen, a tumor-associated antigen, an alloantigen or a viral vector antigen, and (ii) a thioredox motif, as a medicament for increasing the activation, cytokine production and cytolytic activity of CD4+ NKT cells in said subject.

An additional advantage of the present invention is related to the very limited degree of polymorphism of the CD1d molecule. This allows the use of single or of a limited number of peptides for the therapy of outbred populations such as human beings or animals. Moreover, NKT cells elicited from one donor could be used for passive transfer in multiple recipients. This very much contrasts with the situation in which peptides are presented by MEW class I or class II molecules, the polymorphism of which precluding the use of single peptides for multiple recipients.

The general structure of NKT cell epitopes contains a hydrophobic residue in positions P1 and P7, with position P4 occupied by an aliphatic chain. Thus, the general structure can eventually be defined as [FWHY]-xx-[ILMV]-xx-[FWHY] in which x stands for any amino acid. In position P1, P4 and P7, any of the listed amino acid can be present. Aminoacids can be natural amino acids or non-natural amino acids. Examples of non-natural aminoacids include D-aminoacids Generally the organic compound with reducing activity is a peptide sequence. Peptide fragments with reducing activity are encountered in thioreductases which are small disulfide reducing enzymes including glutaredoxins, nucleoredoxins, thioredoxins and other thiol/disulfide oxidoreductases They exert reducing activity for disulfide bonds on proteins (such as enzymes) through redox active cysteines within conserved active domain consensus sequences: C-XX-C, C-XX-S, C-XX-T, S-XX-C, T-XX-C (Fomenko et al. (2003)

*Biochemistry* 42, 11214-11225), in which X stands for any amino acid. Such domains are also found in larger proteins such as protein disulfide isomerase (PDI) and phosphoinositide-specific phospholipase C. In particular, the immunogenic peptides comprise as redox motif the thioreductase sequence motif [CST]-XX-[CST], in a further embodiment thereto, said [CST]-XX-[CST] motif is positioned N-terminally of the T-cell epitope. More specifically, in said redox motif at least one of the [CST] positions is occupied by a Cys; thus the motif is either [C]-XX-[CST] or [CST]-XX-[C]. In the present application such a tetrapeptide will be referred to as "the motif" or "redox motif". More in particular, the immunogenic peptides can contain the sequence motif [C]-XX-[CS] or [CS]-XX-[C]. Even more particularly, the immunogenic peptides contain the sequence motif C-XX-S, S-XX-C or C-XX-C.

The motif in the above immunogenic peptides is placed either immediately adjacent to the epitope sequence within the peptide, or is separated from the T cell epitope by a linker. More particularly, the linker comprises an amino acid sequence of 7 amino acids or less. Most particularly, the linker comprises 1, 2, 3, or 4 amino acids. Typical amino acids used in linkers are serine and threonine. Examples of peptides with linkers in accordance with the present invention are C-XX-C-G-epitope, C-XX-C-GG-epitope C-XX-C-SSS-epitope C-XX-C-SGSG-epitope and the like. In yet another particular embodiment the linker sequence encompasses aminoacids naturally present in the polypeptide sequence from which the CD1d-binding motif is derived. Variable numbers of such natural aminoacids can be included on either the amino- or carboxyterminal ends of the peptide or on both ends.

The immunogenic peptides can comprise additional short amino acid sequences N or C-terminally of the (artificial) sequence comprising the NKT cell epitope and the reducing compound (motif). Such an amino acid sequence is generally referred to herein as a 'flanking sequence'. A flanking sequence can be positioned N- and/or C-terminally of the redox motif and/or of the T-cell epitope in the immunogenic peptide. When the immunogenic peptide comprises an endosomal targeting sequence, a flanking sequence can be present between the epitope and an endosomal targeting sequence and/or between the reducing compound (e.g. motif) and an endosomal targeting sequence. More particularly a flanking sequence is a sequence of up to 10 amino acids, or of in between 1 and 7 amino acids, such as a sequence of 2 amino acids. More particularly, the flanking sequence contains bulky aminoacid residues which are useful to stabilize the peptide into the CD1d molecule.

In particular embodiments of the invention, the redox motif in the immunogenic peptide is located N-terminally from the epitope.

As detailed above, the immunogenic peptides comprise a reducing motif as described herein linked to a NKT cell epitope sequence. In particular cases, the NKT-cell epitopes are derived from proteins which do not comprise within their native natural sequence an amino acid sequence with redox properties within a sequence of 11 amino acids N- or C-terminally adjacent to the NKT-cell epitope of interest.

In particular embodiments, the NKT-cell epitope is derived from an intracellular pathogen. Such pathogens can be viruses, bacteria or parasites. Viruses include ssDNA, dsDNA and RNA viruses, with as examples Herpesviridae, Flaviviridae and Picornaviridae, influenza, measles and immunodeficiency viruses. Bacteria and mycobacteria include *mycobacterium tuberculosis*, other mycobacteria pathogenic for humans or animals, *Yersiniosis, Brucella, Chlamydiae, Mycoplasma, Rickettsiae, Salmonellae* and *Shigellae*. Parasites include *Plasmodiums, Leishmanias, Trypanosomas, Toxoplasma gondii, Listeria, Histoplasma*.

In particular embodiments, the NKT-cell epitope is derived from autoantigens, including thyroglobulin, thyroid peroxidase, TSH receptor in thyroid diseases; insulin (pro-insulin), glutamic acid decarboxylase (GAD), tyrosine phosphatase IA-2, heat-shock protein HSP65, islet-specific glucose6-phosphatase catalytic subunit related protein (IGRP) in type 1 diabetes; 21-OH hydroxylase in autoimmune adrenalitis; 17-alpha hydroxylase, histidine decarboxylase, tryptophan hydroxylase, tyrosine hydroxylase, in autoimmune polyendocrine syndromes; H+/K+ ATPase intrinsic factor in autoimmune gastritis and pernicious anemia; myelin oligodendrocyte glycoprotein (MOG), myelin basic protein (MBP), proteolipid protein (PLP) in multiple sclerosis; acetyl-choline receptor in myasthenia gravis; retinol-binding protein (RBP) in autoimmune ocular syndromes; type II and type IX collagen in autoimmune inner ear diseases; tissue transglutaminase in celiac disease; pANCA histone H1 protein in inflammatory bowel diseases; heat-shock protein HSP60 and oxy-light density lipoproteins in atherosclerosis, and; synuclein in Parkinson disease.

In particular embodiments, the NKT-cell epitope is derived from allofactors, including any peptide or polypeptide used: (1) for replacement therapy for coagulation defects or fibrinolytic defects, including factor VIII, factor IX and staphylokinase; (2) hormones such as growth hormone or insulin; (3) cytokines and growth factors, such as interferon-alpha, interferon-gamma, GM-CSF and G-CSF; (4) antibodies for the modulation of immune responses, including anti-IgE antibodies in allergic diseases, anti-CD3 and anti-CD4 antibodies in graft rejection and a variety of autoimmune diseases, anti-CD20 antibodies in non-Hodgkin lymphomas; (5) erythropoietin in renal insufficiency and; (6) genetically modified antigens.

In particular embodiments, the NKT-cell epitope is derived from allergens, including airborne allergens such as those derived from house dust mite, from pollens or from domestic animals, food allergens such as peanut, ovalbumin, cereals, fruits and legumes, and contact allergens such as latex. Diseases characterizing allergen sensitization include allergic asthma, allergic rhino-sinusitis, anaphylactic shock, urticaria, atopic dermatitis and contact dermatitis.

In particular embodiments, the NKT-cell epitope is derived from tumor, including any peptide or polypeptide derived from: (1) oncogenes, such as the MAGE identified in some melanomas; (2) proto-oncogenes, such as cyclin D1 expressed on soft tissues carcinomas such as those of the kidney or parathyroid, as well as in multiple myeloma; (3) virus-derived proteins, such as those from the Epstein-Barr virus in some carcinomas and in some Hodgkin-type lymphomas; (4) surviving factors, which are anti-apoptotic factors such as survivin or bcl2; (5) clonotypic determinants, such as idiotypic determinants derived from B cell receptor in follicular lymphomas or multiple myelomas or T cell receptor determinants in T cell malignancies In particular embodiments, the NKT-cell epitope is derived from alloantigen, including any peptide or polypeptide derived from major histocompatibility class I or class II determinants, minor histocompatibility complexes or tissue-related antigens. Said peptides or polypeptides can be involved in the rejection of cellular or solid organs. Cellular grafts include cord blood cell graft, stem cell graft, or pancreatic islet cell graft. Solid organ grafts include kidneys, lungs, hearts, livers, pancreas, bones, skin, or soft tissues.

In particular embodiments, the NKT-cell epitope is derived from a viral vector used for gene therapy or gene vaccination, including any peptide or polypeptide of RNA viruses (gamma-retroviruses and lentiviruses) or DNA viruses (adenoviruses, adeno-associated viruses, herpes viruses and poxviruses).

NKT cells elicited and activated by immunogenic peptides of the present invention can suppress pathogenesis due to even complex antigens. A minimum requirement for such cells to be activated is to recognize a cognate peptide presented by the CD1d molecule, leading to killing of the pathogen-loaded cell, or killing of the APC presenting the autoantigen, the allofactor or the allergen, or killing of tumor cells, or killing of APC presenting the alloantigen, or APC presenting the antigen derived from a viral vector.

In all the above situations, said immunogenic peptides activate the production of cytokine, such as IFN-gamma, which will activate other effector cells including CD4+ T cells and CD8+ T cells. Both CD4+ and CD8+ T cells can participate in the elimination of the cell presenting the intracellular pathogen, autoantigen, allofactor, allergen, tumor antigen, alloantigen or antigen derived from viral vector.

In situations in which more than one antigen is present in a subject, the same APC may not present all relevant antigens, as such antigens may be taken up by potentially different APC. It is therefore anticipated that combination of two or more immunogenic peptides may be used for the prevention or treatment of disease. It should be clear for the one skilled in the art that any combination of said immunogenic peptides is envisioned. Examples of such combination include peptides to suppress the production of antibodies to an allofactor such as factor VIII of the coagulation pathway and peptides for the suppression of immune responses to viral vectors used for gene therapy of hemophilia A (absence of functional factor VIII). Other examples include combination of infections with pathogens such as HIV and mycobacterial infections.

Immunogenic peptides for use in the context of the present invention are identified by methods known from the person skilled in the art. In a preferred embodiment, peptides comprising the general sequence [FWHY]-xx-[ILMV]-xx-[FWHY] can be identified. Said peptides are identified by methods known by those skilled in the art using algorithms accessible on line. For instance, peptides can be identified by entering a sequence on the following website: expasy.ch/tools/scanprosite/.

Peptides can then be produced by synthesis using for instance the fmoc solid phase synthesis well known in the art.

However, the general sequence provided here should be considered as an indication that a peptide contains a CD1d binding motif. Said peptides should then be tested in vitro for reactivity with NKT cells. To this end, CD1d+ APC are prepared from either an animal or human source. The cells are then incubated with the peptide of interest and a source of NKT cells. Activation of the later can be identified by proliferation, production of cytokines such as IFN-gamma and IL-4 and surface markers. These methods are well described in the art. In addition, tetramers of the CD1d molecule can be used after loading with the peptide of the invention to detect NKT cells specific for such peptide. One possibility is to use fluorescence-labeled tetramers and detection using a fluorescence sorting system (facs).

The immunogenic peptides of the invention can be produced by recombinant technology using expression systems such as bacterial cells, yeast cells, insect cells, plant cells or mammalian cells.

According to the present invention medicaments are envisaged for the treatment of infection with intracellular pathogens, for the treatment of autoimmune diseases, of immune responses to allofactors or to allergens, for the treatment of tumors, the treatment of graft rejection, or the treatment of immune responses to viral vectors used for gene therapy or gene vaccination. In many of these situations, the treatment can be envisioned as a preventive therapy. The medicament of the invention is usually, though not necessarily, a (pharmaceutical) formulation comprising as active ingredient at least one of the immunogenic peptides of the invention, a population of NKT cells for said immunogenic peptides or a gene therapeutic vector capable of expressing said immunogenic peptide. Apart from the active ingredient(s), such formulation will comprise at least one of a (pharmaceutically acceptable) diluent, carrier or adjuvant. In particular, the pharmaceutical composition of the invention is vaccines for prophylactic or therapeutic application.

According to the present invention medicaments are envisaged for the treatment of autoimmune diseases, the treatment of immune responses to allofactors, the treatment of allergic diseases, the treatment of tumors, the treatment of graft rejection and the treatment of immune responses elicited against viral vectors used for gene therapy and for gene vaccination.

Accordingly, the invention relates to immunogenic peptides, which comprise at least one NKT-cell epitope of a pathogen-associated antigen, an autoantigen, an allergen, an allofactor, a tumor antigen, an antigen shed from a graft or derived from a viral vector used in gene therapy or gene vaccination, coupled to a thioreductase motif of sequence [CST]-XX-[CST].

The aminoterminal cysteine in the motif exerts a nucleophilic attack on a disulfide bridge on a target protein. The disulfide bridge is reduced and an electron exchange with the second cysteine of the motif releases the target protein in a reduced form, which is followed by isomerization and/or homodimerization of the target protein. In some cases heterodimerization can occur by electron exchange with a different protein. The end result is either a change in target protein configuration (isomerization) or formation of dimers or higher order polymers. This mechanism is provided here as an example without any limiting intention.

The NKT cell epitope and the thioreductase motif are optionally separated by a linker sequence. In further optional embodiments the immunogenic peptide additionally comprises an endosome targeting sequence (e.g. late endosomal targeting sequence) and/or additional "flanking" sequences.

As explained in detail further on, the immunogenic peptides of the present invention can be made by chemical synthesis, which allows the incorporation of non-natural amino acids. Accordingly, the cysteine residues of the thioreductase motif can be replaced by another amino acid with a thiol group such as mercaptovaline, homocysteine or other natural or non-natural amino acids with a thiol function. In order to have reducing activity, cysteine residues should not occur as part of a cysteine disulfide bridge. Nevertheless, cysteine residues can be modified such as through methylation, as methylated cysteine is converted into cysteine with free thiol groups in vivo.

In the immunogenic peptides of the present invention comprising the thioreductase motif described above, said motif is located such that, when the epitope fits into the CD1d groove, said motif remains outside of the CD1d binding groove. Said motif is placed either immediately adjacent to the epitope sequence within the peptide, or is separated from the T cell epitope by a linker. More particularly, the linker comprises an amino acid sequence of 7 amino acids or less. Most particularly, the linker comprises 1, 2, 3, or 4 amino acids. In those particular embodiments of the peptides of the invention where the said motif is adjacent to the epitope sequence this is indicated as position P-4 to P-1 or P+1 to P+4 compared to the epitope sequence. Apart from a peptide linker other organic compounds can be used as linker to link the parts of the immunogenic peptide to each other.

In particular embodiments of the invention, the thioreductase motif in the immunogenic peptide is located N-terminally from the epitope.

As described above the immunogenic peptides according to the invention comprise, in addition to a thioreductase motif, a NKT cell epitope derived from a pathogen-associated antigen, an auto- or allofactor, an allergen, a tumor-derived antigen, an antigen shed by a graft or an antigen derived from viral vectors used in gene therapy or gene vaccination. A NKT cell epitope in a protein sequence can be identified by functional assays and/or one or more in silico prediction assays. The amino acids in a NKT cell epitope sequence are numbered according to their position in the binding groove of the CD1d proteins. In particular embodiments, the NKT-cell epitope present within the peptides of the invention consists of between 7 and 25 amino acids, yet more particularly of between 7 and 16 amino acids, yet most particularly consists of 7, 8, 9, 10, 11, 12, 13, 14, 15 or 16 amino acids. In a more particular embodiment, the NKT cell epitope consists of a sequence of 7 amino acids. In a further particular embodiment, the NKT-cell epitope is an epitope, which is presented to NKT cells by CD1d molecules. In particular embodiments of the present invention, the NKT cell epitope sequence is an epitope sequence which fits into the cleft of a CD1d protein, more particularly a 7 aminoacid peptide fitting into the CD1d cleft. The NKT cell epitope of the immunogenic peptides of the invention can correspond either to a natural epitope sequence of a protein or can be a modified version thereof, provided the modified NKT cell epitope retains its ability to bind within the CD1d cleft, similar to the natural NKT cell epitope sequence. The modified NKT cell epitope can have the same binding affinity for the CD1d protein as the natural epitope, but can also have a lowered affinity. In particular embodiments the binding affinity of the modified peptide is no less than 10-fold less than the original peptide, more particularly no less than 5 times less. It is a finding of the present invention that the peptides of the present invention have a stabilizing effect on protein complexes. Accordingly, the stabilizing effect of the peptide-CD1d complex compensates for the lowered affinity of the modified epitope for the CD1d molecule.

In particular embodiments, the immunogenic peptides of the invention further comprise an amino acid sequence (or another organic compound) facilitating uptake of the peptide into (late) endosomes for processing and presentation within CD1d determinants. The late endosome targeting is mediated by signals present in the cytoplasmic tail of proteins and correspond to well-identified peptide motifs such as the dileucine-based [DE]XXXL[LI] or DXXLL motif (e.g. DXXXLL), the tyrosine-based YXXØ motif or the so-called acidic cluster motif. The symbol Ø represents amino acid residues with a bulky hydrophobic side chains such as Phe, Tyr and Trp. The late endosome targeting sequences allow for processing and efficient presentation of the antigen-derived T cell epitope by CD1d molecules. Such endosomal targeting sequences are contained, for example, within the gp75 protein (Vijayasaradhi et al. (1995) *J Cell Biol* 130, 807-820), the human CD3 gamma protein, the HLA-BM ß (Copier et al. (1996) *J. Immunol.* 157, 1017-1027), the cytoplasmic tail of the DEC205 receptor (Mahnke et al. (2000) *J Cell Biol* 151, 673-683). Other examples of peptides which function as sorting signals to the endosome are disclosed in the review of Bonifacio and Traub (2003) *Annu. Rev. Biochem.* 72, 395-447. Alternatively, the sequence can be that of a subdominant or minor T cell epitope from a protein, which facilitates uptake in late endosome without overcoming the NKT cell response towards the pathogen-associated derived NKT cell epitope, the auto- or allofactor derived NKT cell epitope, allergen-derived NKT cell epitope, tumor antigen-derived NKT cell epitope, or NKT cell epitopes derived from alloantigens shed by grafts or antigens from viral vectors used in gene therapy or gene vaccination.

In further particular embodiments, the immunogenic peptides of the invention are peptides comprising NKT cell epitopes which do not comprise a thioreductase motif within their natural sequence. However, in alternative embodiments, a NKT cell epitope binding to the CD1d cleft may comprise a thio-oxidoreductase motif such as described herein within its epitope sequence; the immunogenic peptides according to the invention comprising such NKT-cell epitope must further comprise another free thio-oxidoreductase motif coupled (adjacent of separated by a linker) N- or C-terminally to the epitope such that the attached residue can ensure the reducing activity (contrary to the thio-oxidoreductase motif present in the epitope, which is buried within the cleft).

Another aspect of the present invention relates to methods for generating immunogenic peptides of the present invention described herein. Such methods include the identification of NKT-cell epitopes from pathogen-associated antigens, from autoantigens or allofactors of interest, allergens, tumor-related antigens, alloantigens shed from grafts or antigens derived from viral vectors used in gene therapy or gene vaccination. Ways for in vitro and in silico identification NKT-cell epitopes are amply known in the art and some aspects are elaborated upon hereafter. Such methods further include the generation of immunogenic peptides of the invention including the identified NKT-cell epitope and a thioreductase motif (with or without linker(s), flanking sequence(s) or endosomal targeting sequence. The generated immunogenic peptides are next assessed for the capability to induce CD4+ NKT cells to pathogen-associated antigen, autoantigens, allofactors, allergens, tumor-derived antigens, alloantigens shed from grafts or antigens derived from viral vectors used for gene therapy or gene vaccination.

Immunogenic peptides according to the invention are generated starting from NKT cell epitope(s) of pathogen-associated antigens, or of autoantigens, or of allofactors, or of allergens, or of tumors, or of alloantigens, or of viral vectors used for gene therapy or gene vaccination.

In particular, the NKT-cell epitope used may be a dominant NKT-cell epitope. The identification and selection of a NKT-cell epitope from a pathogen-associated antigen, from an autoantigen, allofactor, an allergen, a tumor-derived antigen, an alloantigen shed by graft or antigens derived from viral vectors used in gene therapy or gene vaccination for use in the context of the present invention is known to a person skilled in the art. For instance, peptide sequences isolated from a pathogen-associated antigen, from an autoantigen or allofactor, an allergen, a tumor-derived antigen, an alloantigen shed by a graft or antigens derived from viral vectors used in gene therapy or gene vaccination are tested by, for example, T cell biology techniques, to determine whether the peptide sequences elicit a NKT cell response. Those peptide sequences found to elicit a NKT cell response are defined as having NKT cell stimulating activity. Human NKT cell stimulating activity can further be tested by culturing NKT cells obtained from an individual sensitized to a pathogen-associated antigen, an autoantigen or allofactor, an allergen, a tumor-derived antigen, an alloantigen shed by graft or antigens derived from viral vectors used in gene therapy or gene vaccination with a peptide/epitope derived from said antigens, and determining whether proliferation of NKT cells occurs in response to the peptide/epitope as measured, e.g., by cellular uptake of tritiated thymidine. Stimulation indices for responses by NKT cells to peptides/epitopes can be calculated as the maximum CPM in response to a peptide/epitope divided by the control CPM. A NKT cell stimulation index (S.I.) equal to or greater than two times the background level is considered "positive." Positive results are used to calculate the mean stimulation index for each peptide/epitope for the group of peptides/epitopes tested. Non-natural (or modified) NKT-cell epitopes can further optionally be tested for their binding affinity to CD1d molecules. The binding of non-natural (or modified) NKT-cell epitopes to CD1d molecules can be performed in different ways. For instance, soluble CD1d molecules are obtained and made tetrameric by synthesis or chemical coupling. The CD1d molecule is purified by affinity chromatography. Soluble CD1d molecules are incubated with a biotin-labeled reference peptide produced according to its strong binding affinity for that CD1d molecule. Peptides to be assessed for CD1d binding are then incubated at different concentrations and their capacity to displace the reference peptide from its CD1d binding is calculated by addition of neutravidin. Methods can be found in for instance Texier et al., (2000) *J. Immunology* 164, 3177-3184). The immunogenic peptides of the invention have a mean NKT cell stimulation index of greater than or equal to 2.0. An immunogenic peptide having a NKT cell stimulation index of greater than or equal to 2.0 is considered useful as a prophylactic or therapeutic agent. More particularly, immunogenic peptides according to the invention have a mean NKT cell stimulation index of at least 2.5, at least 3.5, at least 4.0, or even at least 5.0. In addition, such peptides typically have a positivity index (P.I.) of at least about 100, at least 150, at least about 200 or at least about 250. The positivity index for a peptide is determined by multiplying the mean NKT cell stimulation index by the percent of individuals, in a population of individuals sensitive to a viral vector antigen (e.g., at least 9 individuals, at least 16 individuals or at least 29 or 30, or even more), who have NKT cells that respond to the peptide (thus corresponding to the SI multiplied by the promiscuous nature of the peptide/epitope). Thus, the positivity index represents both the strength of a NKT cell response to a peptide (S.I.) and the frequency of a NKT cell response to a peptide in a population of individuals sensitive to a viral vector antigen. In order to determine optimal NKT cell epitopes by, for example, fine mapping techniques, a peptide having T cell stimulating activity and thus comprising at least one T cell epitope as determined by T cell biology techniques is modified by addition or deletion of amino acid residues at either the N- or C-terminus of the peptide and tested to determine a change in NKT cell reactivity to the modified peptide. If two or more peptides which share an area of overlap in the native protein sequence are found to have human NKT cell stimulating activity, as determined by T cell biology techniques, additional peptides can be produced comprising all or a portion of such peptides and these additional peptides can be tested by a similar procedure. Following this technique, peptides are selected and produced recombinantly or synthetically. NKT cell epitopes or peptides are selected based on various factors, including the strength of the NKT cell response to the peptide/epitope (e.g., stimulation index) and the frequency of the NKT cell response to the peptide in a population of individuals.

Methods used for the identification of a pathogen-associated antigen, from an autoantigen or allofactor, an allergen, a tumor-derived antigen, an alloantigen shed by graft or antigens derived from viral vectors used in gene therapy or gene vaccination are known in the art. Thus, positional cloning or expression cloning strategies can be used to identify candidate antigens. For full description of the methodology, see for instance Mendoza et al, Immunity, 7: 461-472, 1997. Alternatively, peptides actually presented by APC in CD1d molecules can be eluted and separated by various chromatography methods. Full description of such methodology will be found in Scott et al, Immunity, 12: 711-720, 2000. Candidate antigens can be screened by one or more in vitro algorithms to identify a NKT cell epitope sequence within an antigenic protein. Suitable algorithms include, but are not limited to those found on the following website:

http://www.expasy.ch/tools/scanprosite/

More particularly, such algorithms allow the prediction within an antigenic protein of one or more peptide sequences which will fit into the groove of a CD1d molecule.

The immunogenic peptides of the invention can be produced by recombinant expression in, e.g., bacterial cells (e.g. *Escherichia coli*), yeast cells (e.g., *Pichia* species, *Hansenula* species, *Saccharomyces* or *Schizosaccharomyces* species), insect cells (e.g. from *Spodoptera frugiperda* or *Trichoplusia ni*), plant cells or mammalian cells (e.g., CHO, COS cells). The construction of the therefore required suitable expression vectors (including further information such as promoter and termination sequences) involves meanwhile standard recombinant DNA techniques. Recombinantly produced immunogenic peptides of the invention can be derived from a larger precursor protein, e.g., via enzymatic cleavage of enzyme cleavage sites inserted adjacent to the N- and/or C-terminus of the immunogenic peptide, followed by suitable purification.

In view of the limited length of the immunogenic peptides of the invention, they can be prepared by chemical peptide synthesis, wherein peptides are prepared by coupling the different amino acids to each other. Chemical synthesis is particularly suitable for the inclusion of e.g. D-amino acids, amino acids with non-naturally occurring side chains or natural amino acids with modified side chains such as methylated cysteine. Chemical peptide synthesis methods are well described and peptides can be ordered from companies such as Applied Biosystems and other companies. Peptide synthesis can be performed as either solid phase peptide synthesis (SPPS) or contrary to solution phase peptide synthesis. The best-known SPPS methods are t-Boc and Fmoc solid phase chemistry which is amply known to the skilled person. In addition, peptides can be linked to each other to form longer peptides using a ligation strategy (chemoselective coupling of two unprotected peptide fragments) as originally described by Kent (Schnolzer & Kent (1992) *Int. J. Pept. Protein Res.* 40, 180-193) and reviewed for example in Tam et al. (2001) *Biopolymers* 60, 194-205.

This provides the tremendous potential to achieve protein synthesis which is beyond the scope of SPPS. Many proteins with the size of 100-300 residues have been synthesized successfully by this method. Synthetic peptides have continued to play an ever-increasing crucial role in the research fields of biochemistry, pharmacology, neurobiology, enzymology and molecular biology because of the enormous advances in the SPPS.

The physical and chemical properties of an immunogenic peptide of interest (e.g. solubility, stability) is examined to determine whether the peptide is/would be suitable for use in therapeutic compositions. Typically this is optimized by adjusting the sequence of the peptide. Optionally, the peptide can be modified after synthesis (chemical modifications e.g. adding/deleting functional groups) using techniques known in the art.

Accordingly, in yet a further aspect, the present invention provides methods for generating pathogen-associated antigen-specific CD4+ NKT cells, or autoantigen- or allofactor-specific CD4+ NKT cells, or allergen-specific CD4+ NKT cells, or tumor antigen-specific CD4+ NKT cells, or CD4+ NKT cells specific for alloantigens shed from grafts, or CD4+ NKT cells specific for antigens from viral proteins used in gene therapy or gene vaccination, either in vivo or in vitro (ex vivo). In particular said NKT cells respond with strong proliferative properties towards any cell presenting said antigens and are obtainable as a cell population. Further, in particular said NKT cells respond with strong suppressive properties towards any cell presenting an auto- or alloantigen, an allergen, antigens shed from graft or derived from viral proteins used in gene therapy or gene vaccination, and are obtainable as a cell population.

The invention extends to such (populations of) antigen-specific CD4+ NKT cells obtainable by the herein described methods.

In one embodiment, methods are provided which comprise the isolation of peripheral blood cells, the stimulation of the cell population in vitro by contacting an immunogenic peptide according to the invention with the isolated peripheral blood cells, and the expansion of the stimulated cell population, more particularly in the presence of IL-2 or IL-15 and IL-7. The methods according to the invention have the advantage that higher numbers of CD4+ NKT cells are produced and that said cells can be generated which are specific for the pathogen-associated antigen, or for the auto- or allo-antigen, the allergen, the tumor-related antigen, the antigens shed from grafts or the antigens from viral proteins used in gene therapy or gene vaccination (by using a peptide comprising an antigen-specific epitope).

In an alternative embodiment, CD4+ NKT cells can be generated in vivo, i.e. by the administration of an immunogenic peptide provided herein to a subject, and collection of CD4+ NKT cells generated in vivo.

The pathogen-associated antigen-specific CD4+ NKT cells obtainable by the above methods are of particular interest for use as a medicament for preventing in a subject morbidity and/or mortality associated with infection with viruses, bacteria or parasites. The autoantigen or allofactor-specific CD4+ NKT cells obtainable by the above methods are of particular interest for use as a medicament for suppressing morbidity and/or mortality associated with auto-immune diseases or reaction against allofactors. The allergen-specific CD4+ NKT cells obtainable by the above methods are of particular interest for use as a medicament for suppressing morbidity and/or mortality associated with allergic diseases. The tumor antigen-specific CD4+ NKT cells obtainable by the above methods are of particular interest for use as a medicament for suppressing morbidity and/or mortality associated with tumors. The graft alloantigen-specific CD4+ NKT cells obtainable by the above methods are of particular interest for preventing graft rejection. The viral protein-specific CD4+ NKT cells obtainable by the above methods are of particular interest for use as a medicament for suppressing morbidity and/or mortality associated with gene therapy or gene vaccination.

For any of the above-described uses of the immunogenic peptides of the invention, said peptides can be replaced by said CD4+ NKT cells. Both the use of allogeneic and autogeneic cells is envisaged. Any method comprising the administration of said antigen-specific CD4+ NKT cells to a subject in need (i.e., for preventing morbidity associated to infection with an intracellular pathogen, preventing or treating morbidity associated with auto-immune diseases, reaction to allofactor, allergen exposure, tumor, graft rejection and reaction against viral vector antigens) is part of the present invention.

The present invention also relates to nucleic acid sequences encoding the immunogenic peptides of the present invention and methods for their use, e.g., for recombinant expression or in gene therapy. In particular, said nucleic acid sequences are capable of expressing an immunogenic peptides of the invention.

The immunogenic peptides of the invention may be administered to a subject in need by using any suitable gene therapy method. In any use or method of the invention for the prevention of morbidity/mortality associated with a pathogen or for the suppression of immune response to an autoantigen or allofactor, immunization with an immunogenic peptide of the invention may be combined with adoptive cell transfer. When combined, said immunization, adoptive cell transfer and gene therapy can be used concurrently, or sequentially in any possible combination.

In gene therapy, recombinant nucleic acid molecules encoding the immunogenic peptides can be used as naked DNA or in liposomes or other lipid systems for delivery to target cells. Other methods for the direct transfer of plasmid DNA into cells are well known to those skilled in the art for use in human gene therapy and involve targeting the DNA to receptors on cells by complexing the plasmid DNA to proteins. In its simplest form, gene transfer can be performed by simply injecting minute amounts of DNA into the nucleus of a cell, through a process of microinjection. Once recombinant genes are introduced into a cell, they can be recognized by the cell normal mechanisms for transcription and translation, and a gene product will be expressed. Other methods have also been attempted for introducing DNA into larger numbers of cells. These methods include: transfection, wherein DNA is precipitated with calcium phosphate and taken into cells by pinocytosis; electroporation, wherein cells are exposed to large voltage pulses to introduce holes into the membrane); lipofection/liposome fusion, wherein DNA is packed into lipophilic vesicles which fuse with a target cell; and particle bombardment using DNA bound to small projectiles. Another method for introducing DNA into cells is to couple the DNA to chemically modified proteins. Adenovirus proteins are capable of destabilizing endosomes and enhancing the uptake of DNA into cells. Mixing adenovirus to solutions containing DNA complexes, or the binding of DNA to polylysine covalently attached to adenovirus using protein crosslinking agents substantially improves the uptake and expression of the recombinant gene. Adeno-associated virus vectors may also be used for gene delivery into vascular cells. As used herein, "gene transfer" means the process of introducing a foreign nucleic acid molecule into a cell, which is commonly performed to enable the expression of a particular product encoded by the gene. The said product may include a protein, polypeptide, anti-sense DNA or RNA, or enzymatically active RNA. Gene transfer can be performed in cultured cells or by direct administration into mammals. In another embodiment, a vector comprising a nucleic acid molecule sequence encoding an immunogenic peptide according to the invention is provided. In particular embodiments, the vector is generated such that the nucleic acid molecule sequence is expressed only in a specific tissue. Methods of achieving tissue-specific gene expression are well known in the art, e.g., by placing the sequence encoding an immunogenic peptide of the invention under control of a promoter, which directs expression of the peptide specifically in one or more tissue(s) or organ(s). Expression vectors derived from viruses such as retroviruses, vaccinia virus, adenovirus, adeno-associated virus, herpes viruses, RNA viruses or bovine papilloma virus, may be used for delivery of nucleotide sequences (e.g., cDNA) encoding peptides, homologues or derivatives thereof according to the invention into the targeted tissues or cell population. Methods which are well known to those skilled in the art can be used to construct recombinant viral vectors containing such coding sequences. Alternatively, engineered cells containing a nucleic acid molecule coding for an immunogenic peptide according to the invention may be used in gene therapy.

It should be clear for the one skilled in the art that the peptide or polypeptide used in gene therapy may be part of the full antigen from which the peptide or polypeptide is derived.

Where the administration of one or more peptides according to the invention is ensured through gene transfer (i.e. the administration of a nucleic acid which ensures expression of peptides according to the invention in vivo upon administration), the appropriate dosage of the nucleic acid can be determined based on the amount of peptide expressed as a result of the introduced nucleic acid.

The medicament of the invention is usually, but not necessarily, a (pharmaceutical) formulation comprising as active ingredient at least one of the immunogenic peptides of the invention, a (population of) CD4+ NKT cells immunogenic peptide or a gene therapeutic vector capable of expressing said immunogenic peptide. Apart from the active ingredient(s), such formulation will comprise at least one of a (pharmaceutically acceptable) diluent, carrier or adjuvant. Typically, pharmaceutically acceptable compounds (such as diluents, carriers and adjuvants) can be found in, e.g., a Pharmacopeia handbook (e.g. US-, European- or International Pharmacopeia). The medicament or pharmaceutical composition of the invention normally comprises a (prophylactically or therapeutically) effective amount of the active ingredient(s) wherein the effectiveness is relative to the condition or disorder to be prevented or treated. In particular, the pharmaceutical compositions of the invention are vaccines for prophylactic or therapeutic application.

The medicament or pharmaceutical composition of the invention may need to be administered to a subject in need as part of a prophylactic or therapeutic regimen comprising multiple administrations of said medicament or composition. Said multiple administrations usual occur sequentially and the time-interval between two administrations can vary and will be adjusted to the nature of the active ingredient and the nature of the condition to be prevented or treated. The amount of active ingredient given to a subject in need in a single administration can also vary and will depend on factors such as the physical status of the subject (e.g., weight, age), the status of the condition to be prevented or treated, and the experience of the treating doctor, physician or nurse.

The term "diluents" refers for instance to physiological saline solutions. The term "adjuvant" usually refers to a pharmacological or immunological agent that modifies (preferably increases) the effect of other agents (e.g., drugs, vaccines) while having few if any direct effects when given by themselves. As one example of an adjuvant aluminum hydroxide (alum) is given, to which an immunogenic peptide of the invention can be adsorbed. Further, many other adjuvants are known in the art and can be used provided they facilitate peptide presentation in CD1d and NKT cell activation. The term "pharmaceutically acceptable carrier" means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. They include any and all solvents, dispersion media, coatings, antibacterial and antifungal agents (for example phenol, sorbic acid, chlorobutanol), isotonic agents (such as sugars or sodium chloride) and the like. Additional ingredients may be included in order to control the duration of action of the active ingredient in the composition. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders. Suitable pharmaceutical carriers for use in said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents. They may also be prepared by micronisation, for instance in view to obtain them in the form of microspheres usually having a diameter of about 1 to 10 μm, namely for the manufacture of microcapsules for controlled or sustained release of the active ingredients.

Immunogenic peptides, homologues or derivatives thereof according to the invention (and their physiologically acceptable salts or pharmaceutical compositions all included in the term "active ingredients") may be administered by any route appropriate to the condition to be prevented or treated and appropriate for the compounds, here the immunogenic proteins to be administered. Possible routes include regional, systemic, oral (solid form or inhalation), rectal, nasal, topical (including ocular, buccal and sublingual), vaginal and parenteral (including subcutaneous, intramuscular, intravenous, intradermal, intraarterial, intrathecal and epidural). The preferred route of administration may vary with for example the condition of the recipient or with the condition to be prevented or treated.

The formulations may conveniently be presented in unit dosage form and may be prepared by any of the methods well known in the art of pharmacy. Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste. A tablet may be made by compression or moulding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein.

A further aspect of the invention relates to isolated immunogenic peptides comprising a NKT-cell epitope from a pathogen-associated antigen, from an autoantigen or allofactor, from an allergen, a tumor-associated antigen, an alloantigen shed from a graft, or antigens from virus used for gene therapy or gene vaccination and, adjacent to said NKT-cell epitope or separated from said NKT-cell epitope by a linker, a thioreductase motif.

Viral vectors for the purpose of gene therapy or gene vaccination are highly amenable to modifications by means of recombinant nucleic acid technology. In view of the above, a skilled person will further easily envisage that the modification to the viral vector NKT-cell epitope as applied in the immunogenic peptides and their uses according to the invention can be introduced immediately in the viral vector itself. As such, vaccination with the immunogenic peptides comprising a NKT cell epitope of a pathogen-associated antigen, an autoantigen or allofactor, an allergen, an antigen associated with tumor, an alloantigen from a graft, or antigens of viral vectors used for gene therapy or gene vaccination and a thioreductase motif (and/or the corresponding gene vaccination and/or the corresponding adoptive cell transfer) may become redundant as the same beneficial effects can be obtained with a modified viral vector. Hence, the invention further encompasses modified viral vectors defined as isolated viral vectors characterized in that at least one NKT-cell epitope present in at least one of the viral vector proteins is modified by insertion in said viral vector protein, adjacent to said NKT-cell epitope or separated from said NKT-cell epitope by a linker, of a thioreductase motif. In one embodiment thereof, said viral vector is further characterized in that said modified NKT-cell epitope is capable of being presented by a CD1d molecule. In another embodiment, said isolated viral vectors are further characterized in that their cell transducing properties are not significantly altered compared to the same viral vector not carrying the NKT-cell epitope modification.

The present invention will now be illustrated by means of the following examples, which are provided without any limiting intention. Furthermore, all references described herein are explicitly included herein by reference.

EXAMPLES

Example 1

Control of Activation of Class II Restricted CD4+ T Cells Specific to Factor VIII by Immunization with a Peptide Containing a CD1d-Restricted T Cell Epitope and a Thioreductase Motif in Flanking Residues BALB/c Factor VIII KO mice (group A) were immunized 4 times at 1 week interval with 50 μg of peptide 2196, which contains a CD1d-restricted NKT cell epitope and a C-XX-C thioreductase motif within flanking residues (SEQ ID NO:1).

SEQ ID NO:1: CGH CGG FTN MFA TWS PSK

Human factor VIII was then injected by the subcutaneous route using 10 IU per injection on 5 occasions separated by one week. Ten days after the last immunization the mice were sacrificed and spleen CD4+ T cells were prepared by magnetic cell sorting. Such cells were stimulated twice with the immunizing peptide and FVIII in vitro before assessing their activation state as measured by the production of IL-4 and IFN-gamma. A control group (B) was treated according to the same protocol but did not receive peptide vaccination.

The results (FIG. 1) show a 10-fold reduction of IL-4 production by Factor VIII specific CD4+ T cells obtained from mice immunized with the peptide as compared to the control group, and a 7-fold reduction in the production of IFN-gamma.

Results are shown as means+SEM.

Example 2

Suppression of Anti-Ad5 IgG Antibody Response by Immunization with a Peptide Containing a CD1d-Restricted NKT Cell Epitope and a Thioreductase Motif C57BL/6 mice (n=6) were immunized by four subcutaneous injections of 50 μg of peptide of SEQ ID NO:2 in alum carried out at one-week interval.

SEQ ID NO:2: CHG CGG FIGLMYY

Such peptide contains a CD1d-restricted NKT cell epitope of hexon protein of adenovirus 5 (Ad5) and a thioreductase motif in flanking residues. A control group (n=6) of mice received physiological serum in alum instead of peptide. All mice then received 2 injections of $10^9$ Ad5 viral particles by the IV route, separated by 1 week. Ten days after the last Ad5 injection, mice were bled and the concentration of total IgG antibodies to Ad5 particles was measured in a direct binding ELISA. Briefly, Ad5 viral particles were insolubilized on polystyrene plates, followed by washing and incubation with a dilution of mouse serum. After a second washing, the binding of mouse anti-Ad5 antibodies was detected by addition of a goat antiserum to mouse IgG. Mice pretreated with peptide (black histogram; FIG. 2) did not produce significant amounts of antibodies, whilst non-immunized mice (open histogram) produce a brisk response after the second Ad5 injection. Results are given in arbitrary units as means+SEM.

** indicates significance at $p<0.001$.

Example 3

Induction of Apoptosis of Tumor Cells by CD4+ NKT Cells Elicited by Mouse Immunization with a Peptide Encompassing a CD1d Restricted NKT Epitope Containing a Thioreductase Motif C57BL/6 mice (n=6) were immunized by four subcutaneous injections of 50 μg of peptide of SEQ ID NO:3 in alum carried out at one-week interval.

SEQ ID NO:3: CGH CGG FDKLPGF

Such peptide contains a CD1d-restricted NKT cell epitope derived from ovalbumin and a thioreductase motif in flanking residues. A control group (n=6) of mice received physiological serum in alum instead of peptide. Ten days after the last immunization the mice were sacrificed and spleen CD4+ T cells were prepared by magnetic cell sorting.

Such cells were stimulated twice with the immunizing peptide in vitro before assessing their activation state as measured by the production of IL-4 and IFN-gamma.

CD4+ NKT cell lines were then assayed in vitro for their capacity to kill EG7 tumor cells. EG7 tumor cells (H-2b) are derived from a thymoma transduced with an ova construct. A CD1d restricted ova epitope is presented by such cells, which is known to be insufficient to trigger NKT activation and tumor cell killing.

EG7 cells were labeled at membrane level with 1 μM $DiOC_{18}$ (3,3'-dioctadecycloxacarbocyanine perchlorate from Invitrogen). EG7 cells ($1 \times 10^5$ per well) were then cultured for 18 h at 37° C. in the presence of NKT cell lines at ratios of 1/1 to 1/5 (EG7 cells versus NKT cells). The NKT cell lines had first been stimulated for 4 h in vitro with antigen-presenting cells loaded with peptide of SEQ ID3. After 18 h, cells were harvested and stained for Annexin V and 7-AAD following manufacturer's instructions (Apoptosis Detection kit; BD Biosciences) and analysed on a FACSCantoII flow cytometer (BD Biosciences).

Results show that EG7 cells incubated with NKT cell lines obtained from mice immunized with peptide of SEQ ID3 are induced into apoptosis, while NKT cells obtained from control mice which have received physiological serum instead of peptide did not induce a significant degree of tumor cell apoptosis.

Example 4

Use of Tetramers of CD1d Molecules for the Detection of MOG-Specific CD4+ NKT Lymphocytes Multiple sclerosis is a chronic demyelination disease wherein CD4+ NKT cells towards auto antigens such as the myelin oligodendrocytic glycoprotein (MOG) are likely to play a key role. Its experimental equivalent, EAE (experimental autoimmune encephalomyelitis) mimic most of human disease hallmarks and is used to understand pathogenetic mechanisms and delineate new treatments.

Enumerating MOG-specific CD4+ NKT cells could therefore be predictive of disease outcome.

A CD1d binding epitope is identified in the mouse MOG protein by combination of algorithms and functional assay as described above, corresponding to sequence 200 to 206.

CD4+ NKT cells are prepared from the spleen of C57BL/6 mice in which EAE has been induced. CD4(-) cells are first removed from the spleen cell suspension using magnetic beads.

Tetramers of CD1d molecules (H-2b) are made as known in the art, including a fluorescent label such as phicoerythrin.

A synthetic peptide is produced, which encompasses a CD1d-restricted MOG NKT cell epitope and a thioreductase motif by incubation overnight:
CGPCGGFLRVPCWKI (SEQ ID NO:4), which contains a linker joining the thioreductase motif (CGPC) and the CD1d binding motif.

Tetramers are loaded with peptide of SEQ ID 4 overnight at room temperature. Loaded tetramers are then washed and incubated with CD4+ T cells for 2 h at 37° C. The suspension is then read with a fluorescence-activated cell sorting system and the proportion of NKT cells specific to the MOG peptide is evaluated.

Example 5

Direct Killing of a H-2b Tumor Cell (R113) by NKT Cells Elicited with a CD1d-Restricted NKT Cell Epitope Derived from Anaplastic Lymphoma Kinase (ALK)

The anaplastic lymphoma kinase is a transmembrane receptor tyrosine kinase that is expressed on many cells during ontogeny, but only on tumors of ectodermal origin in adult life. It is therefore considered as an oncogen directly related to all tumors of ectodermal origin as shown in both animal models and human tumors. For example, up to 60% of human breast cancers express ALK. ALK+ tumor cell lines of mouse origin are available and can be used to evaluate whether ALK-specific cytolytic CD4+ T cells of the invention are able to kill tumor cells.

CD4 T cells (C57BL/6, H-2b background) obtained from the spleen of nave mice were stimulated four times with autologous dendritic cells loaded with a CD1d-restricted NKT cell epitope of ALK, to which a thioreductase motif of the CxxC format was added within flanking residues. (Peptide <u>CHGC</u>GGWLQIVTWWGPGS (SEQ ID NO:5) (with thioreductase motif underlined and 2 glycines used as linker between the motif and the CD1d-restricted epitope)).

As NKT cells have per se a cytolytic activity, we included cells which were stimulated in parallel experiments by exposure to the same CD1d-restricted NKT epitope in natural sequence, without thioredox motif (WLQIVTWWGPGS) (SEQ ID NO: 9).

Ten days after the last stimulation, CD4 T cells were washed and added to cell culture microplates containing $10^4$ R113 tumor cells at a 2 to 1 ratio (CD4 to tumor cells). R113 is a tumor B cell line obtained from C57BL/6 mice, which constitutively expresses ALK.

After 20 h of co-culture, R113 tumor cells were evaluated for Annexin V binding used as marker of cell apoptosis.

Figure 3:
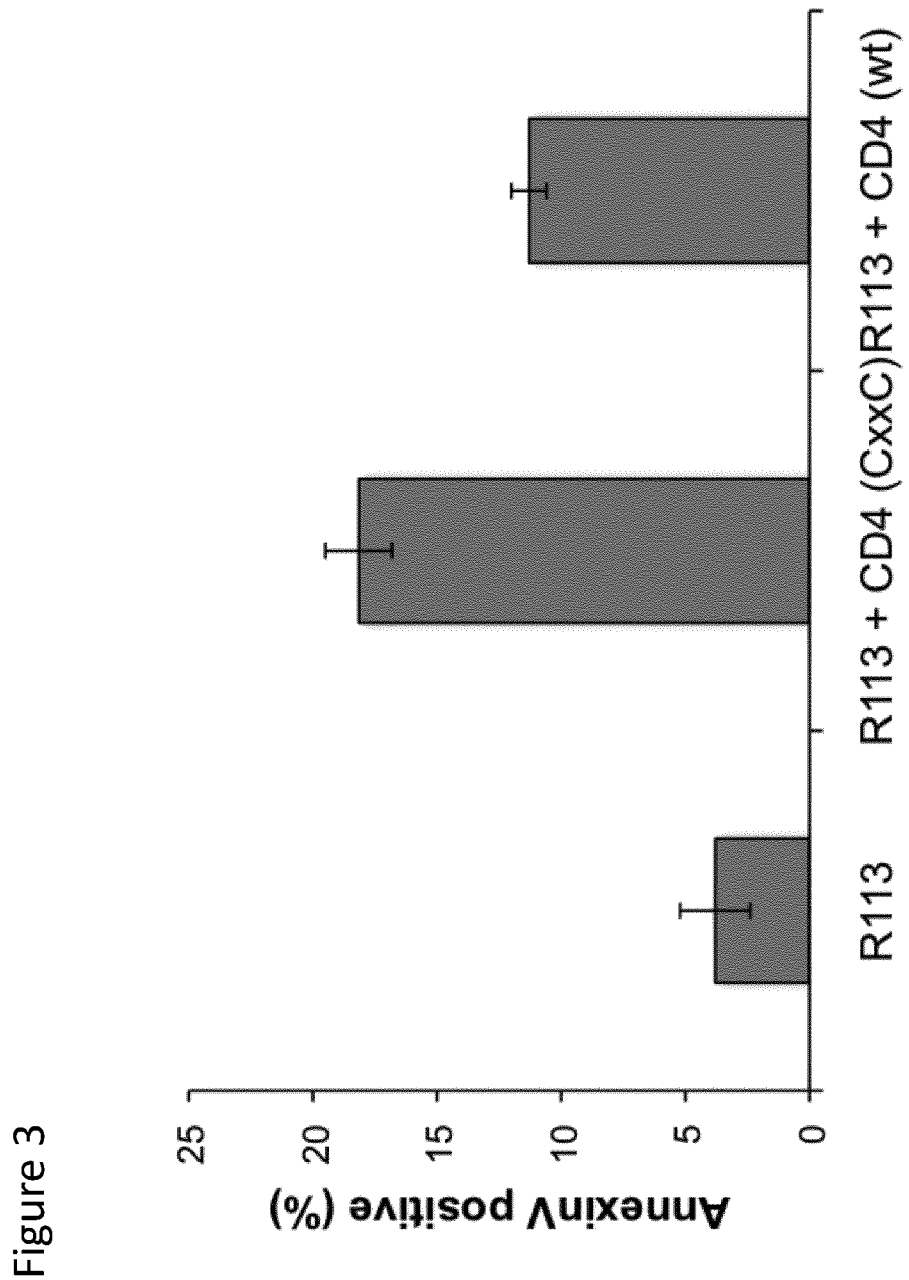

FIG. 3 shows that in the presence of NKT cells cultured with peptide of sequence 1, there is a 4.5-fold increase in tumor cell death (18%; middle histogram) as compared to tumor cells cultured alone (3.8%; left histogram). As expected, NKT cells activated by cognate interaction with CD1d and the peptide in natural sequence show an intermediate % of cell death (11%, right histogram). mean±SD of triplicates.

It is therefore concluded that:
(1) peptides can be presented within the context of CD1d determinants;
(2) bona fide tumor cells can be induced into apoptosis by exposure to NKT cells obtained by activation through cognate recognition of a CD1d-restricted epitope;
(3) a significantly higher proportion of tumors cells are induced into apoptosis when NKT cells are activated by exposure to a CD1d-restricted NKT cell epitope containing a thioreductase motif within flanking residues.

In a second experiment, naive CD4 T cells from an alternative genetic background (BALB/c mice, H-2d background) were obtained from the spleen of naïve mice and were stimulated four times with autologous dendritic cells loaded with peptide of SEQ ID5.

Co-culture with a BALB/c-derived ALK+ tumor cell line (VAC) was carried out as described above. Apoptosis of tumor cells was measured by evaluating Annexin-V binding by faccs.

Figure 4:
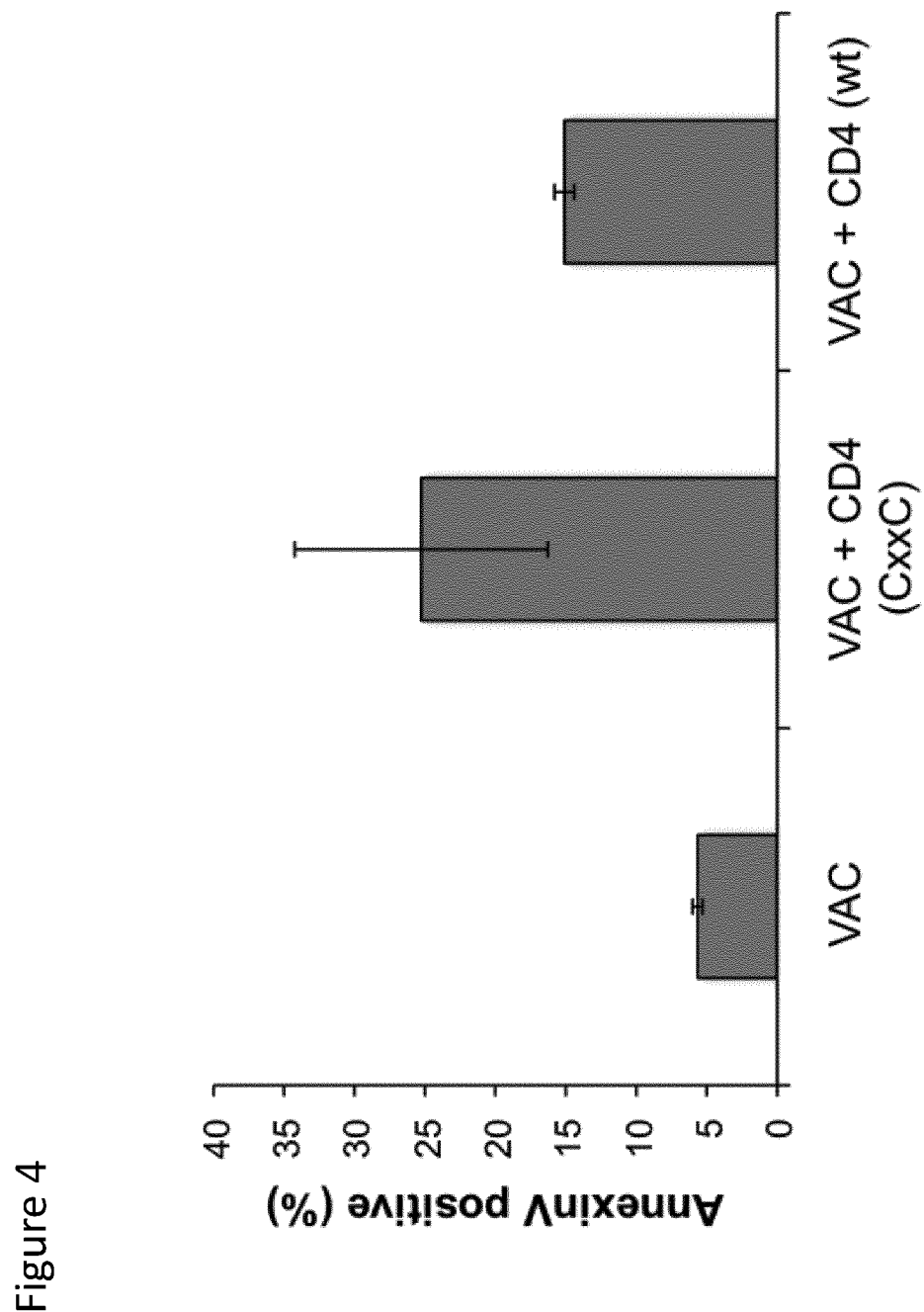

FIG. 4 shows that in the presence of NKT cells cultured with peptide of sequence 1, there is a significant increase in tumor cell death (25%; middle histogram) as compared to tumor cells cultured alone (5.6%; left histogram) or in the presence of peptide in natural sequence (15%; right histogram). mean±SD of triplicates These data indicate that a second, unrelated tumor cell line can be induced into apoptosis when exposed to NKT cells, and that this effect is significantly increased when NKT cells have been stimulated by exposure to CD1d-restricted epitopes containing a thioreductase motif within flanking residues.

Example 6

Prevention of EAE by Pre-Immunization with a Peptide Containing a CD1d Binding and a Thioreductase Motif EAE (experimental autoimmune encephalomyelitis) is a model disease in which central nervous system demyelination occurs and which is considered as the experimental equivalent of multiple sclerosis. A small number of autoantigens are considered to be implicated in the elicitation and maintenance of disease, among which the MOG (myelin oligodendrocytic glycoprotein). Disease can be elicited in the C57BL/6 mice by MOG immunization, using a CD4+ T cell epitope encompassing MOG aminoacids 35-55.

MOG contains a sequence which binds to CD1d and activates NKT cells. Thus, peptide of sequence PHFLRVPCWKI (SEQ ID NO:10) is produced by synthesis and a thioreductase-containing peptide of sequence CHGCGGFLRVPCWKI (peptide of SEQ ID NO:6, in which the thioreductase motif is underlined and a linker of 2 glycines between the motif and the CD1d-binding motif).

Groups of C57BL/6 mice are immunized four times subcutaneously (50 µg) with peptide of SEQ ID6 or, as a control, with peptide in natural sequence. Ten days after the last immunization, all mice, including a group of naïve, non-immunized animals, are induced into disease by subcutaneous injection of 100 µg MOG 35-55 peptide/400 µg *Mycobacterium butyricum* in CFA and ip injection of 300 ng *Bortetella pertussis* in NaCl. At day +2, a second injection of *B. pertussis* is given.

Signs of EAE are followed over time. It is observed that mice pre-immunized with peptide of SEQ ID6 do not develop EAE, whilst the control naïve mice and the group pre-immunized with peptide in natural sequence develop significant disease signs.

Example 7

Prevention and Suppression of Spontaneous Insulin-Dependent Diabetes with GAD65 Derived Peptides Non-obese diabetes (NOD) mice constitute a suitable animal model for spontaneous insulin-dependent diabetes. In such animals, as in human beings, an early immune response to the autoantigen glutamic acid decarboxylase (GAD65) is observed at a time at which insulitis can be seen, from which the response extends by intramolecular and intermolecular spreading. Inducing tolerance to GAD65 by administration of the protein to neonates prevents the onset of diabetes.

GAD65 contains amino acid sequences with the capacity to bind to CD1d. Thus, the sequence PQHTNVCFWFV (SEQ ID NO:11), corresponding to amino acids 501 to 507 of GAD65, is produced by synthesis, as well as its counterpart encompassing a thioreductase motif within flanking residues: peptide of CHGCGGHTNVCFWFV (SEQ ID NO:7) (with the thioreductase motif underlined and a linker of 2 glycines between the motif and the CD1d binding motif).

Female NOD mice are immunized from the age of 4 weeks by 4 subcutaneous injections of peptides of either SEQ ID7 or natural sequence, and glycaemia is followed in each of these groups, by comparison to a non-immunized group. It is observed that NOD mice pre-immunized with peptide of SEQ ID7 are prevented from hyperglycaemia, whilst mice treated with peptide of natural sequence and non-immunized animals develop hyperglycaemia starting after the 14$^{th}$ week.

Example 8

Prevention of Asthma Induced by Exposure to an Allergen, Der p 1

Allergens from the house dust mite, *D. pteronyssinus*, are frequently involved in allergic asthma. Der p 1 is the main allergen of *D. pteronyssinus*. The sequence of Der p 1 contains a CD1d binding motif corresponding to aminoacid sequence 38 to 44. A peptide of sequence WAFSGVAATES (SEQ ID NO:12) is produced by synthesis as well as its counterpart containing a thioreductase motif. Thus, peptide CGPCGGFSGVAATES (SEQ ID NO:8) contains a thioreductase motif (underlined) and a linker of 2 glycines between the motif and the CD1d-binding motif.

Allergic asthma can be induced in BALB/c mice by nasal instillations of 100 µg Der p 1 administered on 3 consecutive days. Asthma is characterized by bronchial hyperreactivity and attraction of eosinophil infiltrates into the lung.

BALB/c mice are immunized by 4 injections of 50 µg of peptides of either SEQ ID8 or peptide in natural sequence as a control. Der p 1 is administered by nasal instillation 10 days after the last immunization. It can be observed that mice preimmunized with peptide of SEQ ID8 do not develop airway reactivity to inhalation of methacholine and do not show lung infiltration with eosinophils.

The invention claimed is:

1. A method for preparing a peptide capable of eliciting NKT cell activation, said method comprising the steps of:
   (1) identifying within an antigenic protein a NKT cell epitope sequence comprising a [FWHY]-xx-[ILMV]-xx-[FWHY] motif, wherein x is any amino acid, and wherein [FWHY] is an amino acid selected from Phe, Trp, His, and Tyr, and wherein [ILMV] is an amino acid selected from Ile, Leu, Met, and Val,
   (2) testing a peptide with a NKT cell epitope sequence identified in step (1) in vitro for activation of NKT cells when said peptide is presented by CD1d, and (3) providing a peptide comprising:

a NKT cell epitope tested in step (2) and having confirmed activation of NKT cells, linked to a thioreductase [CST]-xx-C or C-xx-[CST] motif, wherein x is any amino acid, and wherein [CST] is an amino acid selected from Cys, Ser, and Thr, such that said thioreductase motif and said NKT cell epitope sequence are either immediately adjacent to each other or separated by a linker of at most 7 amino acids in length.

2. The method according to claim 1, wherein said antigenic protein is selected from the group consisting of an autoantigen, an allofactor, an allergen, a tumor associated antigen, an alloantigen shed by a graft, an antigen from a viral vector used for gene therapy or gene vaccination, and an intracellular pathogen associated antigen.

3. The method according to claim 1, wherein said thioreductase motif and said NKT cell epitope are either immediately adjacent to each other or separated by a linker of at most 4 amino acids in length.

4. The method according to claim 1 wherein said antigenic protein does not comprise a [CST]-xx-C or C-xx-[CST] motif within 11 amino acids N- or C terminally adjacent to said NKT cell epitope.

5. The method according to claim 1, comprising in step (1) identifying within an antigenic protein a NKT cell epitope sequence comprising a [FW]-xx-[ILMV]-xx-[FW] motif, wherein [FW] is Phe or Trp.

6. The method according to claim 1, comprising in step (1) identifying within an antigenic protein a NKT cell epitope sequence comprising a [FW]-xx-[ILM]-xx-[FW] motif, wherein [ILM] is an amino acid selected from Ile, Leu, and Met.

7. The method according to claim 1, wherein said thioreductase motif is C-xx-C.

8. The method according to claim 7, wherein x stands for any amino acid except tyrosine, phenylalanine, and tryptophan.

* * * * *

SEQUENCE LISTING

```
<160> NUMBER OF SEQ ID NOS: 12

<210> SEQ ID NO 1
<211> LENGTH: 18
<212> TYPE: PRT
<213> ORGANISM: Artificial Sequence
<220> FEATURE:
<223> OTHER INFORMATION: Synthetic Construct

<400> SEQUENCE: 1

Cys Gly His Cys Gly Gly Phe Thr Asn Met Phe Ala Thr Trp Ser Pro
1               5                   10                  15
```

Ser Lys

<210> SEQ ID NO 2
<211> LENGTH: 13
<212> TYPE: PRT
<213> ORGANISM: Artificial Sequence
<220> FEATURE:
<223> OTHER INFORMATION: Synthetic Construct

<400> SEQUENCE: 2

Cys His Gly Cys Gly Gly Phe Ile Gly Leu Met Tyr Tyr
1               5                   10

<210> SEQ ID NO 3
<211> LENGTH: 13
<212> TYPE: PRT
<213> ORGANISM: Artificial Sequence
<220> FEATURE:
<223> OTHER INFORMATION: Synthetic Construct

<400> SEQUENCE: 3

Cys Gly His Cys Gly Gly Phe Asp Lys Leu Pro Gly Phe
1               5                   10

<210> SEQ ID NO 4
<211> LENGTH: 15
<212> TYPE: PRT
<213> ORGANISM: Artificial Sequence
<220> FEATURE:
<223> OTHER INFORMATION: Synthetic Construct

<400> SEQUENCE: 4

Cys Gly Pro Cys Gly Gly Phe Leu Arg Val Pro Cys Trp Lys Ile
1               5                   10                  15

<210> SEQ ID NO 5
<211> LENGTH: 18
<212> TYPE: PRT
<213> ORGANISM: Artificial Sequence
<220> FEATURE:
<223> OTHER INFORMATION: Synthetic Construct

<400> SEQUENCE: 5

Cys His Gly Cys Gly Gly Trp Leu Gln Ile Val Thr Trp Trp Gly Pro
1               5                   10                  15

Gly Ser

<210> SEQ ID NO 6
<211> LENGTH: 15
<212> TYPE: PRT
<213> ORGANISM: Artificial Sequence
<220> FEATURE:
<223> OTHER INFORMATION: Synthetic Construct

<400> SEQUENCE: 6

Cys His Gly Cys Gly Gly Phe Leu Arg Val Pro Cys Trp Lys Ile
1               5                   10                  15

<210> SEQ ID NO 7
<211> LENGTH: 15
<212> TYPE: PRT
<213> ORGANISM: Artificial Sequence
<220> FEATURE:
<223> OTHER INFORMATION: Synthetic Construct

<400> SEQUENCE: 7

```
Cys His Gly Cys Gly Gly His Thr Asn Val Cys Phe Trp Phe Val
1               5                   10                  15

<210> SEQ ID NO 8
<211> LENGTH: 15
<212> TYPE: PRT
<213> ORGANISM: Artificial Sequence
<220> FEATURE:
<223> OTHER INFORMATION: Synthetic Construct

<400> SEQUENCE: 8

Cys Gly Pro Cys Gly Gly Phe Ser Gly Val Ala Ala Thr Glu Ser
1               5                   10                  15

<210> SEQ ID NO 9
<211> LENGTH: 12
<212> TYPE: PRT
<213> ORGANISM: Artificial Sequence
<220> FEATURE:
<223> OTHER INFORMATION: Synthetic Construct

<400> SEQUENCE: 9

Trp Leu Gln Ile Val Thr Trp Trp Gly Pro Gly Ser
1               5                   10

<210> SEQ ID NO 10
<211> LENGTH: 11
<212> TYPE: PRT
<213> ORGANISM: Artificial Sequence
<220> FEATURE:
<223> OTHER INFORMATION: Synthetic Construct

<400> SEQUENCE: 10

Pro His Phe Leu Arg Val Pro Cys Trp Lys Ile
1               5                   10

<210> SEQ ID NO 11
<211> LENGTH: 11
<212> TYPE: PRT
<213> ORGANISM: Artificial Sequence
<220> FEATURE:
<223> OTHER INFORMATION: Synthetic Construct

<400> SEQUENCE: 11

Pro Gln His Thr Asn Val Cys Phe Trp Phe Val
1               5                   10

<210> SEQ ID NO 12
<211> LENGTH: 11
<212> TYPE: PRT
<213> ORGANISM: Artificial Sequence
<220> FEATURE:
<223> OTHER INFORMATION: Synthetic Construct

<400> SEQUENCE: 12

Trp Ala Phe Ser Gly Val Ala Ala Thr Glu Ser
1               5                   10
```